United States Patent
Jones et al.

(10) Patent No.: US 9,024,259 B2
(45) Date of Patent: May 5, 2015

(54) METHOD AND APPARATUS FOR ELECTROMAGNETIC DETECTION FOR USE IN THE MANUFACTURE OF FIBROUS WEB

(75) Inventors: Philip Coleman Jones, Dedham (GB); Antony Douglas Hartell, Chelmsford (GB)

(73) Assignee: NDC Infrared Engineering Limited, Essex (GB)

( * ) Notice: Subject to any disclaimer, the term of this patent is extended or adjusted under 35 U.S.C. 154(b) by 1045 days.

(21) Appl. No.: 12/673,333

(22) PCT Filed: Aug. 12, 2008

(86) PCT No.: PCT/GB2008/002729
§ 371 (c)(1),
(2), (4) Date: Jun. 7, 2011

(87) PCT Pub. No.: WO2009/022126
PCT Pub. Date: Feb. 19, 2009

(65) Prior Publication Data
US 2011/0303848 A1 Dec. 15, 2011

(30) Foreign Application Priority Data
Aug. 13, 2007 (EP) .................................... 07253181

(51) Int. Cl.
*G01N 21/47* (2006.01)
*G01N 21/3563* (2014.01)
(Continued)

(52) U.S. Cl.
CPC ............ *G01N 21/47* (2013.01); *G01N 21/3563* (2013.01); *G01N 21/359* (2013.01); *G01N 21/86* (2013.01); *G01N 21/8915* (2013.01); *G01N 2021/8917* (2013.01); *G01N 21/3559* (2013.01)

(58) Field of Classification Search
CPC ..... G01N 21/359; G01N 21/35; G01N 21/47; G01N 21/3559; G01N 21/3554; G01N 21/8915; G01N 21/86; G01N 21/8917

USPC ......... 250/559.01, 340, 338.1, 338.9, 559.07, 250/559.08, 559.11, 559.15
See application file for complete search history.

(56) References Cited

U.S. PATENT DOCUMENTS 3,828,173 A * 8/1974 Knepler .......................... 702/28
4,948,260 A * 8/1990 Felix et al. .................... 356/429
(Continued)

FOREIGN PATENT DOCUMENTS

| JP | 48-42953 | 12/1973 |
|---|---|---|
| JP | 5-87733 | 4/1993 |

(Continued)

OTHER PUBLICATIONS

International Search Report for parent application PCT/GB2008/002729, having a mailing date of Nov. 5, 2008.
(Continued)

*Primary Examiner* — Yara B Green
(74) *Attorney, Agent, or Firm* — Andrus Intellectual Property Law, LLP

(57) ABSTRACT

An apparatus for measuring parameters, such as moisture content or basis weight, of a fibrous web, e.g. paper or non-wovens, comprises optical elements and a wavelength selection device for selectively directing a beam of electromagnetic radiation comprising wavelengths in at least the mid infrared (MIR) spectral range through the web; an element, such as a beam stop, arranged in the path of electromagnetic radiation emerging from the web, for separating directly transmitted from scattered electromagnetic radiation; a collector for collecting the scattered radiation; and at least one detector for detecting the scattered radiation collected by the collector.

16 Claims, 19 Drawing Sheets

(51) Int. Cl.
*G01N 21/359* (2014.01)
*G01N 21/86* (2006.01)
*G01N 21/89* (2006.01)
*G01N 21/3559* (2014.01)

(56) References Cited

U.S. PATENT DOCUMENTS

2001/0028459 A1 10/2001 Hartenstein et al.
2004/0042011 A1 3/2004 Moshe
2005/0106312 A1 5/2005 Mantyla

FOREIGN PATENT DOCUMENTS

| WO | 9901748 | 1/1999 |
| WO | 01/59435 A | 8/2001 |
| WO | 03/087814 A | 10/2003 |

OTHER PUBLICATIONS

European Search Report for priority application EP 07253181, having a completion date of Nov. 30, 2007.

Office Action in corresponding Japanese Patent Application No. 2010-520620, mailed Nov. 6, 2012.

Office Action in corresponding Chinese Patent Application No. 200880103193.6, mailed Jun. 23, 2011.

* cited by examiner

METHOD AND APPARATUS FOR ELECTROMAGNETIC DETECTION FOR USE IN THE MANUFACTURE OF FIBROUS WEB

CROSS-REFERENCE TO RELATED APPLICATIONS

This application is the U.S. national stage application of International Application No. PCT/GB2008/002729, filed Aug. 12, 2008, which International application was published on Feb. 19, 2009, as International Publication No. WO 2009/022126 A1 in the English language, which application is incorporated herein by reference. The International application claims priority of European Patent Application No. 07253181.7, filed Aug. 13, 2007, which application is incorporated herein by reference.

BACKGROUND

The present invention relates to a method and apparatus for electromagnetic detection, particularly to such method and apparatus for use in the measurement of at least one parameter of a fibrous web during manufacture.

The invention has particular application in the manufacture of fibrous webs, such as paper or non-woven sheet material, for use in the medical and hygiene industries. In particular, the invention may be employed for on-line measurement of a parameter, e.g. the moisture content and/or the basis weight, of a fibrous web for providing a control output, e.g. for process or quality control, during web manufacture.

The invention at least in its preferred form described below employs infrared measurement techniques and detectors in the manufacture of fibrous web.

In the specification, the term "parameter" is used to denote the property (moisture content, thickness, basis weight etc.) being measured, the term "sample" is used to denote the portion of the object (substrate, sheet, web etc.) presented to the measurement gauge for measurement, and the term "fibrous web" covers all forms of sheet material comprising fibres compacted together, including paper and non-wovens.

A variety of measurement gauges have previously been employed in the paper and non-woven industries, in processes for continuously manufacturing fibrous web, in order to detect various parameters of the web. For example, it is extremely important to know the weight per unit area of the fibrous web as it is produced, since the density or basis weight of the web may be closely correlated with its ultimate tensile strength, burst strength and water transmittance. It is also extremely important in these industries to monitor the moisture content of the web as it is treated, in order to ensure drying efficiency and the sterility of the ultimate product.

However, the existing techniques in these industries for measuring basis weight and moisture content, including those employing infrared absorption spectroscopy, have hitherto proved unsatisfactory. The interaction of light with the small fibres and voids in the fibrous web is very complex, and this can cause serious measurement issues, particularly in the case of lightweight webs typically having a weight in the range 8-20 gsm and a fibre size of 10-20 μm. For example, light striking the web in the region of the voids will tend to pass through the web with little or no interaction, so that the measurement detector picks up only a faint absorption signature from the target web. And, in the region of the fibres, the light striking the web interacts strongly with the fibres and is scattered, and may often be diverted away from the measurement detector altogether.

Further, the inclusion amongst the measurement signals of signals obtained from light passing straight through the voids and signals obtained from light scattered away from the measurement detector significantly distorts the measurements obtained, and in some cases may result in the generation of a wholly inaccurate spectral absorption characteristic pattern. Such issues are particularly pronounced in the case of lightweight materials where the proportion of voids to fibrous mass is much greater.

Hitherto, no satisfactory measurement gauge has been found to measure parameters of lightweight fibrous web material.

In other industries, infrared absorption gauges are well known and are used for measuring various constituents or parameters of samples or substrates, such as the moisture content of the sample, the thickness or coating weight of a film on a base layer or substrate, or the thickness or basis weight of the sample.

Infrared absorption gauges conventionally operate by projecting infrared radiation at two or more wavelengths onto a sample and measuring the intensity of the radiation reflected, transmitted or scattered by the sample. Signals proportional to the measured intensity are processed to provide a value of the parameter being measured. At least one of the two or more wavelengths projected by the gauge is chosen to be absorbed by the parameter of interest, while at least one other wavelength is chosen to be substantially unaffected by the parameter of interest. For example, when measuring the amount of water in a sample, one of the wavelengths (the "measuring wavelength") can be chosen at an absorption wavelength of water (either 1.45 micrometer (microns) or 1.94 micrometer (microns)) and the other wavelength (known as the "reference wavelength") is chosen to be one that is not significantly absorbed by water.

Generally, gauges include an infrared radiation source having a predetermined emission spectrum, and a detector for receiving radiation reflected, transmitted or scattered by the sample; filters are placed between the source and the sample to expose the sample only to the desired measuring and reference wavelengths; in this case, the sample is successively exposed to radiation at the selected wavelengths, e.g. by placing appropriate filters on a rotating wheel in front of the radiation source. Alternatively, a filter wheel can be placed between the sample and the detector, and each filter be successively interposed between the sample and the detector.

The detector measures the intensity of light after interaction with the sample and produces a signal according to the intensity of the radiation incident upon it. In the most simple case, by calculating the ratio between the signal from the detector when receiving light at the measuring wavelength and the signal from the detector when receiving light at the reference wavelength, a measurement signal can be obtained that provides a measure of the parameter concerned, for example the amount of moisture in the sample. Often, several measuring wavelengths and/or several reference wavelengths are used, and the signals of the measuring wavelengths and of the reference wavelengths are used to calculate the parameter concerned.

Such infrared absorption gauges have been proposed for use in the manufacture of fibrous web, but only partially successfully and only in the case of medium and heavyweight materials.

Tests on a lightweight fibrous web, using a standard measurement gauge employing light in the near infrared (NIR) range of 1-2.5 μm and scatter based measurement, found that the measurements obtained were overly sensitive to fillers, fibre size and fibre distribution to produce a robust measurement. At the same time, tests with a standard direct transmission measurement gauge employing light in the near infrared (NIR) and mid infrared (MIR) ranges of 1-4 µm found that the measurement data was very variable and unreliable as a result of the effects of fibre size and web voids.

Thus, significant measurement problems exist in the use of standard infrared measurement gauges in the manufacture of fibrous web, both in the case of direct transmission light and scattered light measurement gauges. Further tests also revealed that measurement problems exist with most fibrous web materials but are particularly pronounced when the web material is a lightweight one.

Accordingly, there is a significant need in the industries for manufacturing fibrous web, such as paper and non-woven sheet material, for a measurement gauge capable of producing accurate measurements of various parameters, irrespective of the weight range of the web and irrespective of the distribution of voids and fibres throughout the web, and especially at the lightweight end of the possible weight ranges where the proportion of voids to fibre mass is high and the fibre density is low.

SUMMARY

The present invention seeks to overcome these problems and to provide a new measurement gauge capable of highly sensitive, accurate and reproducible measurement.

For the sake of clarity, in this invention, near infrared (NIR) wavebands may be considered to be those generally in the range 1-2.5 µm, mid infrared (MIR) wavebands may be considered to be those generally in the range 2.5-5 µm, medium weight and heavyweight fibrous webs may be considered to be those having basis weights in excess of 30 gsm and lightweight fibrous webs may be considered to be those having a basis weight in the range 5-30 gsm and a fibre size up to 20 µm.

According to one aspect of the invention, there is provided a method of measuring at least one parameter of a fibrous web, comprising:
  directing a beam of electromagnetic radiation towards the fibrous web;
  passing the beam of electromagnetic radiation through the fibrous web;
  selecting wavelengths for the electromagnetic radiation by means of a wavelength selection device;
  differentiating electromagnetic radiation emerging from the fibrous web into directly transmitted electromagnetic radiation that constitutes electromagnetic radiation substantially directly transmitted through the fibrous web and scattered electromagnetic radiation that constitutes electromagnetic radiation scattered by interaction with the fibrous web;
  collecting the scattered electromagnetic radiation; and
  detecting the collected electromagnetic radiation and generating electrical signals representing the radiation received;
  wherein the range of wavelengths selected by the wavelength selection device for the elctromagnetic radiation that is subsequently collected and detected for generating electrical signals includes wavelengths in the mid infrared (MIR) range of 2.5-5 µM.

According to another aspect of the invention, there is provided detection apparatus for use for measuring at least one parameter of a fibrous web, comprising:
  optical elements for directing a beam of electromagnetic radiation towards the fibrous web;
  a wavelength selection device for selecting wavelengths for the electromagnetic radiation;
  an optical system for differentiating electromagnetic radiation that emerges from the fibrous web into directly transmitted electromagnetic radiation that constitutes electromagnetic radiation substantially directly transmitted through the fibrous web and scattered electromagnetic radiation that constitutes electromagnetic radiation scattered by interaction with the fibrous web;
  said optical system including an element arranged in the path of electromagnetic radiation emerging from the fibrous web for separating directly transmitted electromagnetic radiation from scattered electromagnetic radiation, and a collector for collecting the scattered electromagnetic radiation; and
  at least one detector for detecting electromagnetic radiation collected by the collector and for generating an electrical signal representing the radiation received;
  wherein the range of wavelengths selected by the wavelength selection device for the electromagnetic radiation detectable by the at least one detector includes wavelengths in the mid infrared (MIR) range of 2.5-5 µM.

In a preferred embodiment of the invention, the range of wavelengths selected by the wavelength selection device includes the near infrared (NIR) range of 1-2.5 um and is extended beyond the NIR range into the mid infrared (MIR) range of 2.5-5 um, and the wavelength selection device is arranged to select wavelengths including at least one wavelength in the NIR range and at least one wavelength in the MIR range.

It has been found that the differentiation of directly transmitted and scattered light for measurement of the scattered light, together with the use of a wavelength range significantly extended beyond the NIR range into the MIR range, has very considerable advantages in providing for consistent, reliable and accurate measurement of parameters, such as moisture content and/or basis weight, even in the case of very lightweight fibrous materials having basis weights in the range 5-30 gsm and a fibre size up to 20 µm.

The scattered electromagnetic radiation is advantageously collected over a wide angle. Preferably, the scattered light passes directly to a collector for collection on emerging from the fibrous web. In one embodiment, following collection, the scattered electromagnetic radiation is directed away from the axis of the beam for detection, for example by employing at least one of an asymmetrical collector and an asymmetrically disposed collector for directing the scattered electromagnetic radiation away from the axis of the beam for detection.

Preferred embodiments of the invention described below measure also the directly transmitted light for providing comparative measurements and removing the effects of interference patterns. As before, the directly transmitted light may be directed away from the transmission axis for detection.

Other preferred embodiments measure the reflected scattered light, which offers the advantages of facilitating surface coating measurement and/or correcting for variations in fibre coverage.

According to another aspect of the invention, there is provided detection apparatus for use for the detection of parameters of a fibrous web, comprising:
  optical elements for directing a beam of electromagnetic radiation towards the fibrous web;
  a wavelength selection device for selecting wavelengths for the electromagnetic radiation;
  an optical direction system for directing electromagnetic radiation after interaction of the electromagnetic radiation beam with the fibrous web; and a plurality of detectors for receiving electromagnetic radiation directed by the optical direction system and for generating electrical signals representing the radiation received;

wherein the optical direction system includes a collector for collecting electromagnetic radiation scattered by the fibrous web as the electromagnetic radiation passes through the fibrous web, one of said plurality of detectors being arranged to receive said scattered electromagnetic radiation from said collector; and wherein the optical direction system further includes at least one other direction arrangement for directing electromagnetic radiation, selected from a direct transmission direction arrangement for electromagnetic radiation that is transmitted along the axis of the beam through the fibrous web and a collector for collecting electromagnetic radiation that is reflected and scattered by the fibrous web as the beam strikes the fibrous web, one or a respective other of said plurality of detectors being associated with the or each said other direction arrangement.

BRIEF DESCRIPTION OF THE DRAWINGS

The invention will now be described further, by way of example, with reference to the accompanying drawings, in which.

DETAILED DESCRIPTION OF THE DRAWINGS

Figure 2:
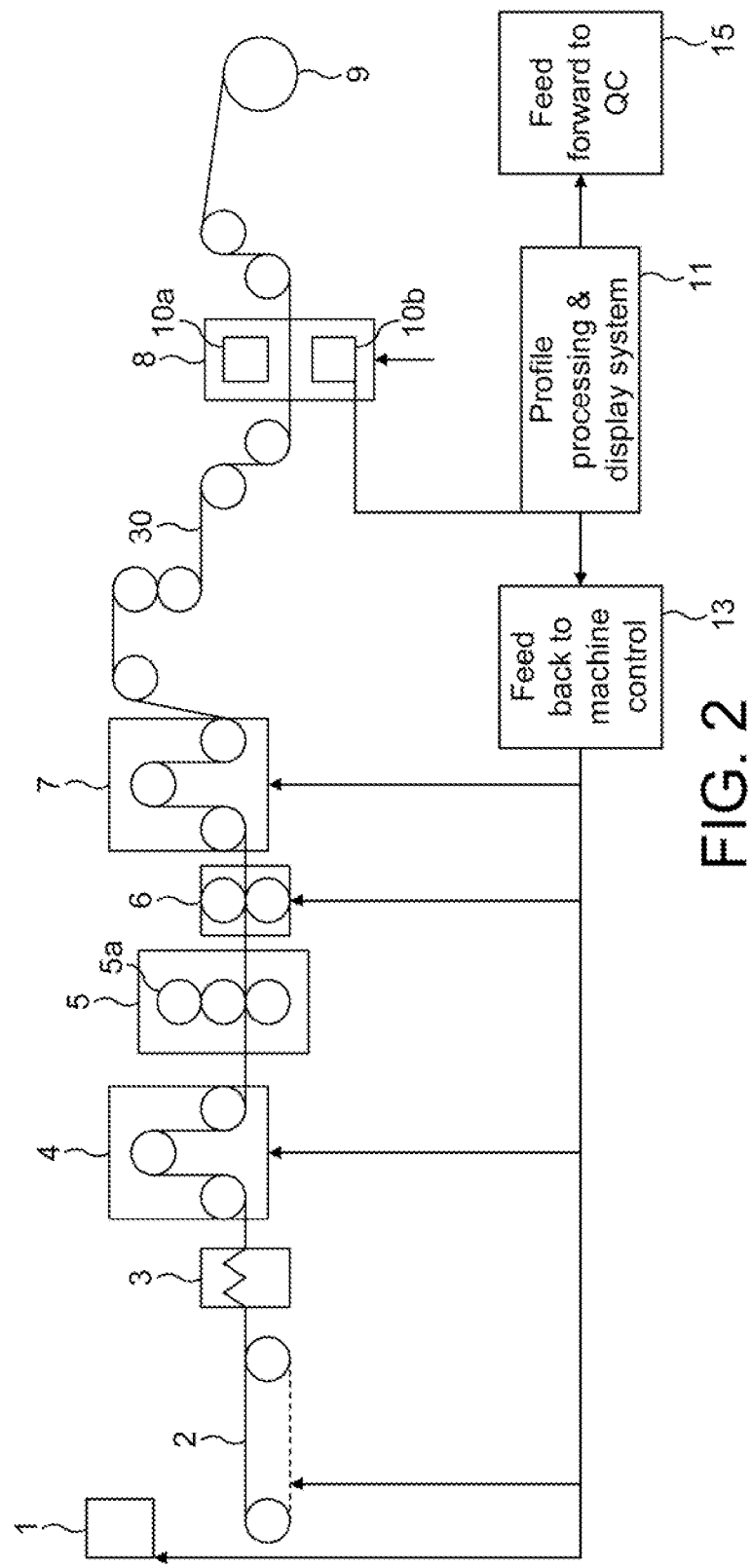
FIG. 2 is a schematic diagram of a conventional fibrous web manufacturing process and system.
Figure 3:
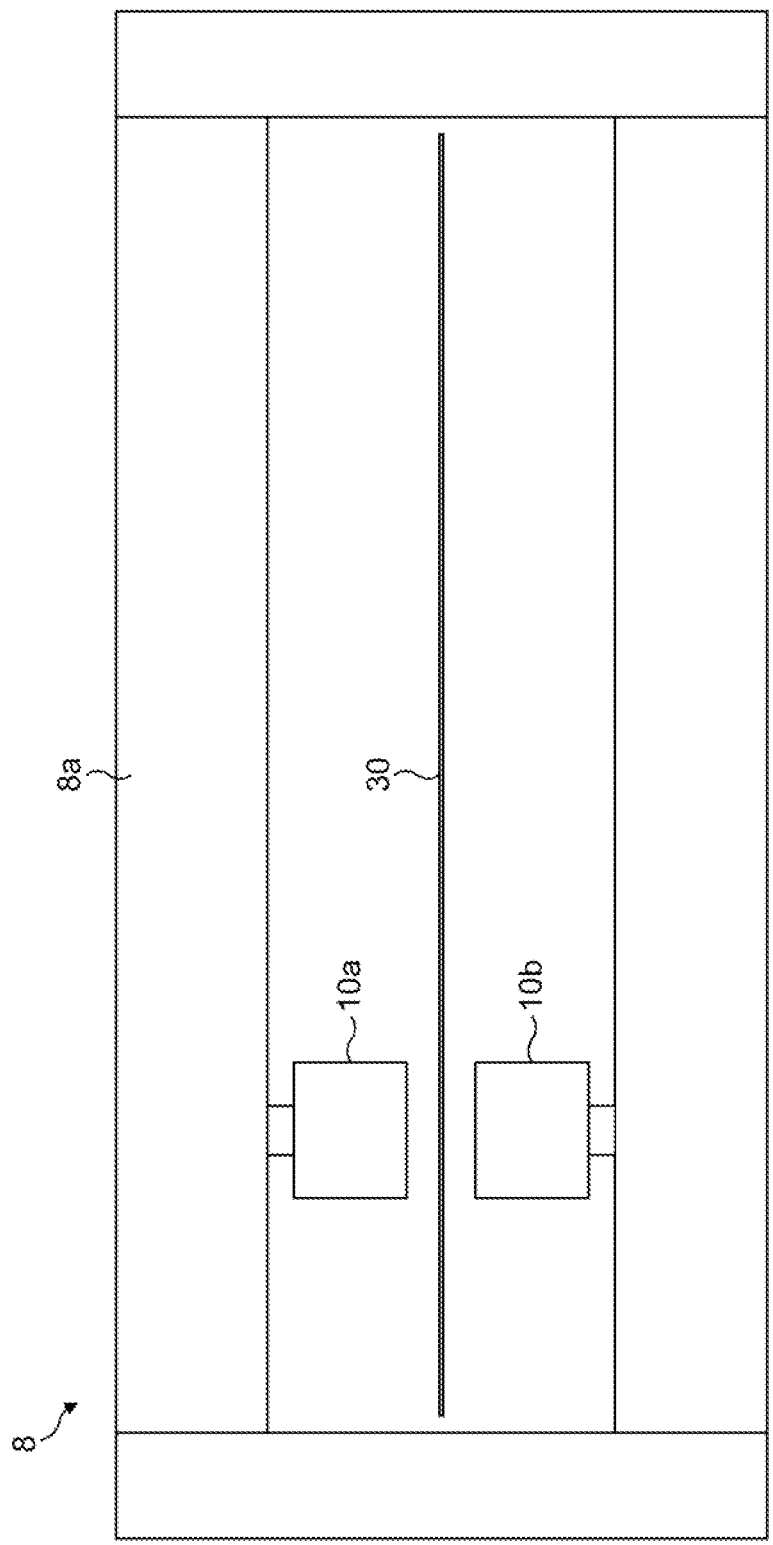
FIG. 3 is a schematic view of a mounting frame for a sensor of the system of FIG. 2.
Figure 4:
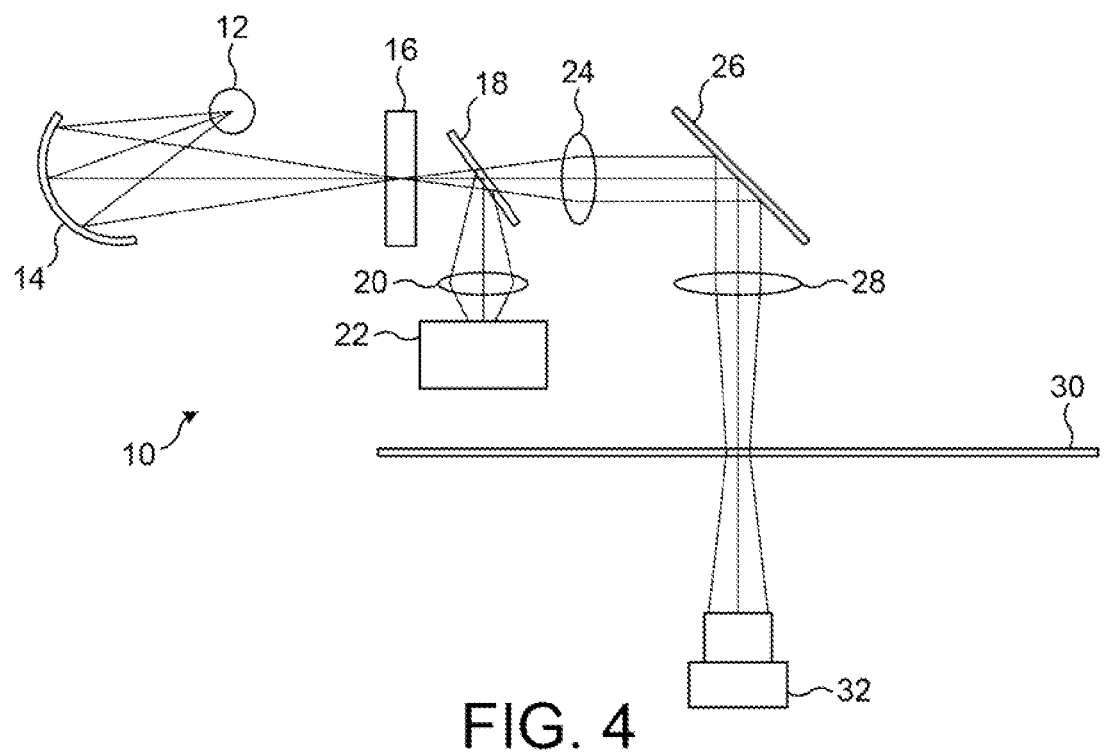
FIG. 4 is a schematic diagram of a conventional infrared transmission sensor.

Referring firstly to FIGS. 2 to 4, a conventional fibrous web manufacturing process and a conventional infrared direct transmission light sensor or measurement gauge will be described by way of explanation.

FIGS. 2 and 3 shows a system for manufacturing a fibrous web, in which fibre supply apparatus 1 deposits and distributes fibres on a moving wire or belt 2. The apparatus 1 may comprise a fibre forming tower containing dies for depositing spun or blown fibres in the form of a fluff layer or layers on the belt 2, in which tower air flow is controlled in order to diffuse the fibres uniformly on the belt 2. Alternatively, the apparatus 1 may comprise bale detangling apparatus 1 for receiving and detangling bales of fibre and distributing them as a fluff layer or layers on the belt 2. The fluff layer(s) is or are supplied to entangling apparatus 3, which may use air and water or mechanical means for entangling the fibres to form a wet felt layer. The wet felt layer is supplied to a dryer 4 for drying and to a calendaring stack 5 of hot rollers 5a to initiate binding into a web 30. The calendaring stack 5 develops the smoothness, patterning and gloss of the web surface using up to sixteen rollers 5a which apply pressure and temperature to the web 30. The web is then supplied to treater/coater/moisturiser apparatus 6 for applying treatments and/or a surface coating and/or for moisturising the web 30, and thence to a dryer 7 for drying the web 30 before passing it through a gauging zone 8 to a winder 9 for winding the web 30 under tension into a roll.

It is to be appreciated that the number of supply apparatuses 1, driers 4, treater/coater/moisturiser apparatuses 6 etc may be varied according to the application. Further, the entangler 3 and the dryer 4 may be omitted in some applications.

During production, the basis weight of the fluff layer(s) on the belt 2, the coating weight produced by the apparatus 6, and the humidity of the web 30 emerging from the dryers 7 is constantly monitored and is adjusted on a continuous basis.

For this purpose, a measurement gauge 10, as shown in FIG. 4, is situated in the gauging zone 8 to detect parameters of the fibrous web, such as basis weight, coating weight and moisture content. The gauge 10 supplies measurement signals to a profile processing and display system 11 where the measurement signals are processed and optionally the results are displayed. Based on the measurement results, the processing system 11 supplies feedback signals to a process control system 13, which applies a control output to one or more of the fibre supply apparatus 1, the belt 2, the dryer 4, the treater/coater/moisturiser 6 and the dryer 7. The processing system 11 also supplies feed forward signals based on the measurement results to a data logging quality control system 15, which processes the results for purposes of quality control in subsequent roll converting processes.

As shown in FIG. 3, the gauging zone 8 comprises a scanning frame 8a extending transversely across the web 30 on both sides to provide a mounting for an upper sensor head 10a and a lower sensor head 10b of the measurement gauge 10. In a conventional manner, the scanning frame 8a includes parallel rails (not shown) on which the heads 10a, 10b are mounted, and a motor (not shown) is conventionally provided for scanning the sensor heads 10a, 10b in synchronism to and fro orthogonally across the width of the web 30 to obtain a cross web measurement profile. In a variation of this arrangement, the heads may be fixed to provide in-line trend data.

A conventional measurement gauge 10 will now be described with reference to FIG. 4.

The known measurement gauge 10 is an infrared gauge including a white light source 12, whose light is directed towards a condenser mirror 14 arranged to focus the light into a beam striking a filter wheel 16. The filter wheel 16 is driven in a conventional manner by a motor (not shown). The filter wheel 16 carries a series of filters, for example 5 filters, and each filter is designed to pass infrared radiation having a different selected narrowband emission waveband in the range of wavelengths 1-4 μm. The light passed by the respective filters is directed towards a beam splitter 18, which reflects a portion of the light beam by way of a lens 20 to a calibration detector 22, and which transmits a portion of the light beam by way of a further lens 24 towards an angled mirror 26. The mirror 26 reflects the light beam through 90 degrees downwardly by way of another lens 28 towards a fibrous web of sheet material 30 whose parameters are being measured. The axis of the light beam is perpendicular to the web 30 and therefore this light beam is transmitted directly through the web 30 and is collected by a transmitted light detector 32 placed on the same axis underneath the web 30. The parts of the measurement gauge 10 shown in FIG. 4 above the web 30 are carried by the head 10a, and those shown below, ie the detector 32, are carried by the head 10b.

Figure 1:
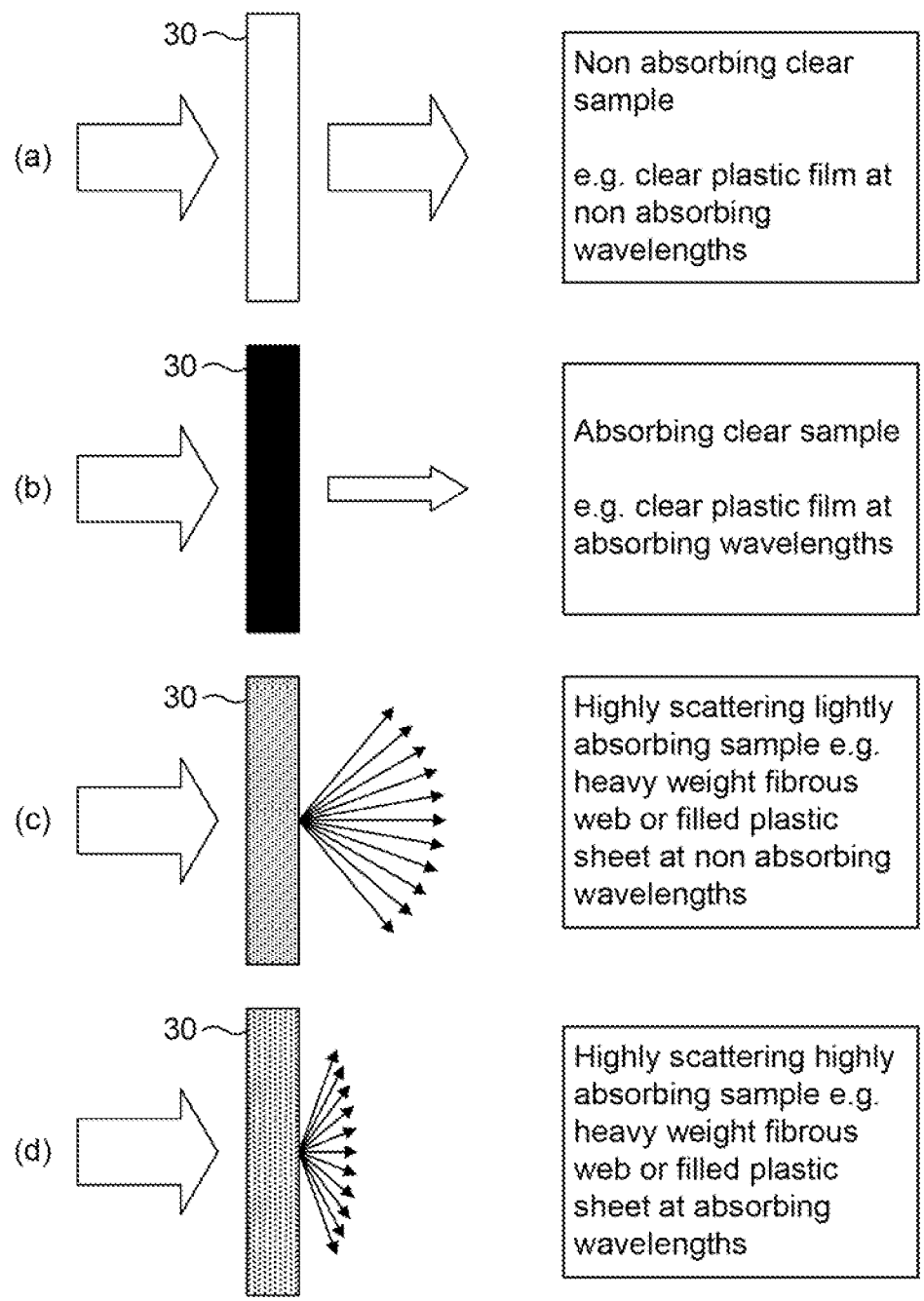
FIGS. 1a to 1f are diagrams representing the effects on a measurement light beam of different kinds of sheet material, for explaining the background to the invention.
Figure 1:
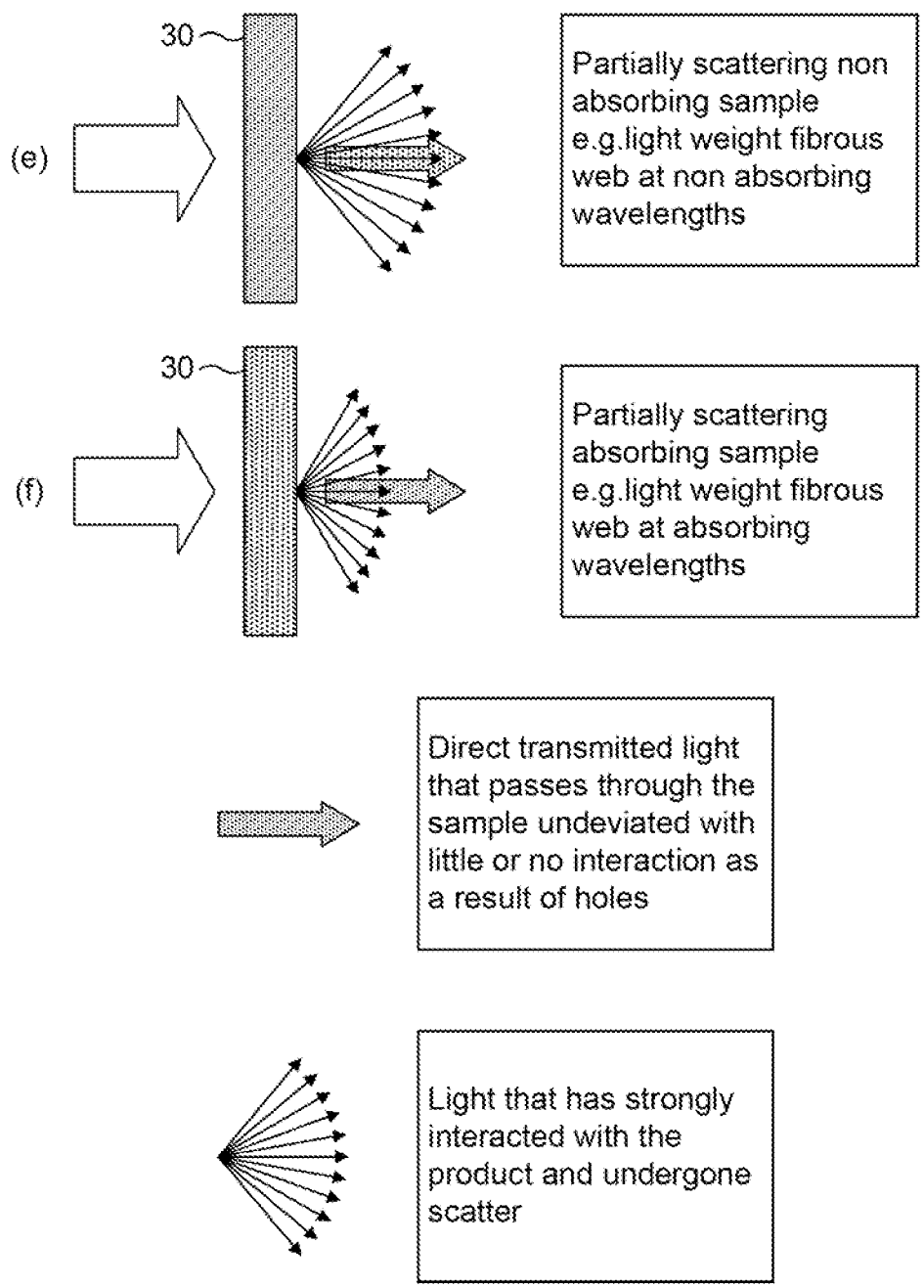

Reverting to FIG. 1, different possible examples of sheet material providing the web 30 are displayed, showing in each case the effect on the projected beam of light as it is transmitted through the web 30.

The material of the web 30 in FIG. 1a and FIG. 1b is a clear plastic film, made by another process than that described with reference to FIGS. 2 and 3, and the projected light in FIG. 1a has a wavelength at which it is not absorbed, whereas the projected light in FIG. 1b has a wavelength at which significant absorption takes place. Accordingly, in the example of FIG. 1a, most of the light passes through the web 30 for collection by the detector 32 and, in the example of FIG. 1b, a substantial proportion of the light is absorbed leaving only a small proportion to be picked up by the detector 32.

The material of the web 30 in FIGS. 1c and 1d is a heavyweight sheet of fibrous material or filled plastics, typically having a basis weight of 60-100 gsm, in which the fibres and fillers have a tendency to scatter the transmitted light. Again, in the example of FIG. 1c, the projected light has a wavelength at which the web 30 does not absorb light, whereas in the example of FIG. 1d the projected light has a wavelength at which a significant proportion of the light is absorbed. As shown, however, in both instances the light is scattered away from the detector 32 with a relatively small proportion of the scattered light in the example of FIG. 1c still reaching the detector 32 and very little of the scattered light at all reaching the detector 32 in the example of FIG. 1d.

Turning to FIGS. 1e and 1f, the material of the web 30 is a lightweight fibrous sheet, typically having a basis weight of 5-30 gsm, which both transmits the projected light directly and scatters the projected light. In the example of FIG. 1e, the projected light has a wavelength at which very little absorption takes place by the web 30, and, in the example of FIG. 1f, the projected light has a wavelength at which the fibres of the web 30 absorb the light. As shown, the proportion of light which is directly transmitted may or may not vary between the example of FIG. 1e and the example of FIG. 1f, the level of absorption of direct transmission light in the example of FIG. 1f being dependent on the proportion of voids to fibre, ie on the hole density of the web. By contrast, the proportion of light which is scattered is closely dependent on the wavelength of the light impinging on the web 30. In the case of the example of FIG. 1e, a proportion of the projected light is scattered but not absorbed while in the example of FIG. 1f the same proportion of light is both scattered and absorbed. Accordingly, in this instance, the proportion of directly transmitted light falling on the detector 32 and affected by the web 30 is uncertain since it is not known whether such light has interacted with the web 30 or not, and the proportion of the projected light which is scattered will to a small extent fall on the detector 32 in the example of FIG. 1e and will barely at all reach the detector 32 in the example of FIG. 1f.

It will be apparent therefore, that the conventional infrared measurement gauge shown in FIG. 4 is highly suitable for measuring parameters associated with a material such as a clear plastic film but is less effective in measuring parameters associated with a heavyweight fibrous web and is hardly effective at all in measuring parameters associated with a lightweight fibrous web.

Figure 5:
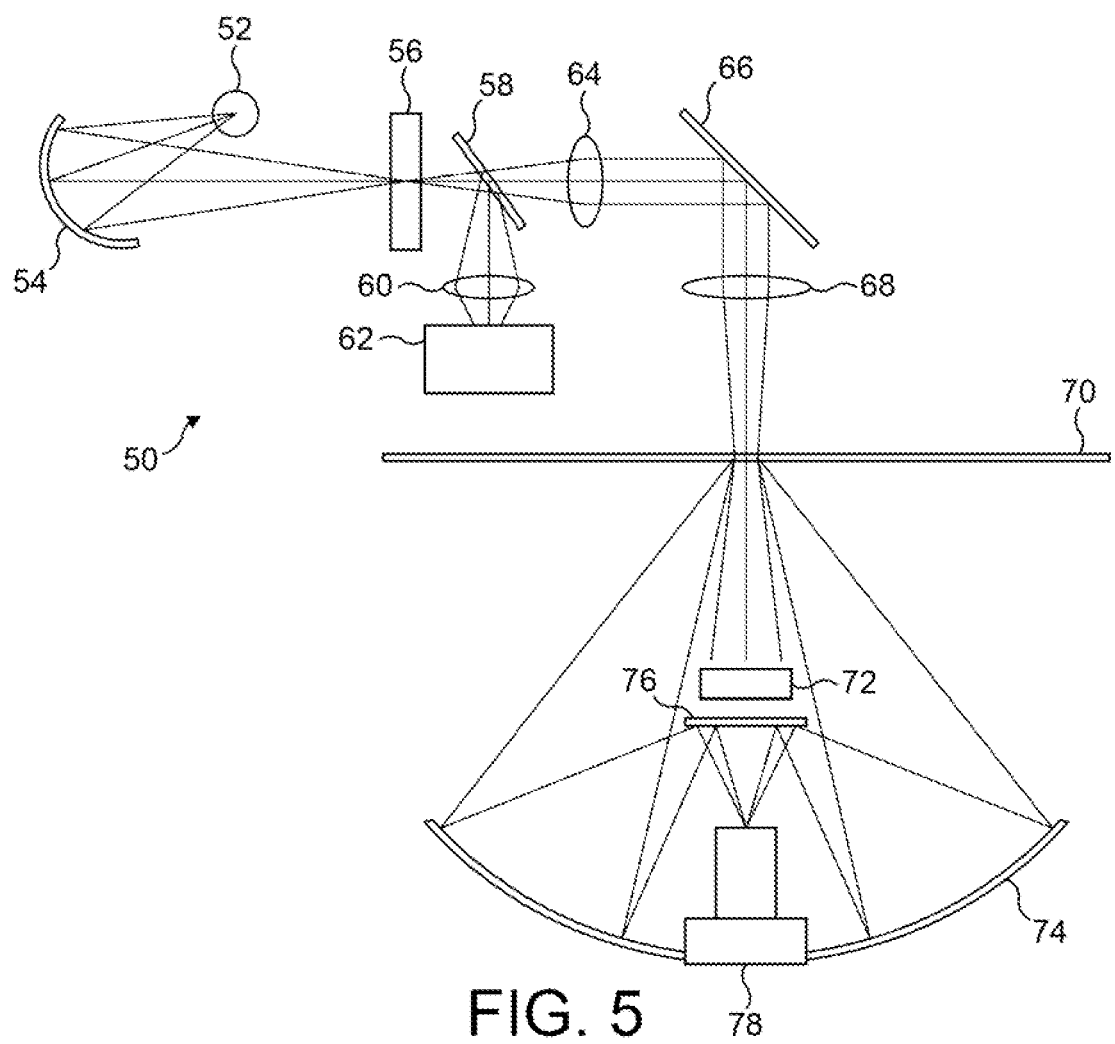
FIG. 5 is a schematic diagram of a first embodiment of the present invention employing a scattered light detector, suitable for use in the system and process of FIGS. 2 and 3.
Figure 6:
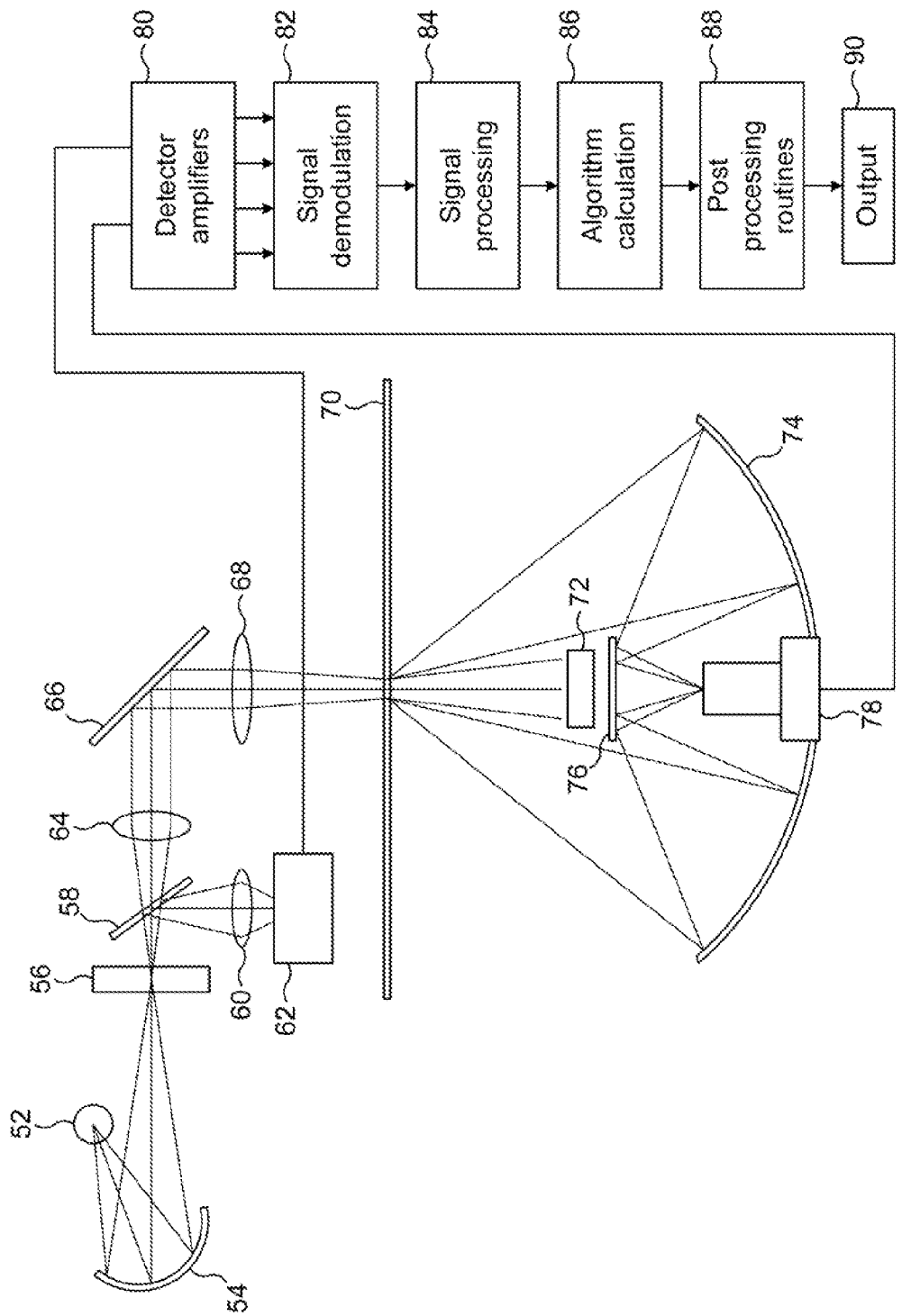
FIG. 6 is a further diagram of the first embodiment showing in block diagram form the circuitry for processing the measurement signals obtained from the detector.

Turning to FIGS. 5 and 6, a first embodiment of measurement gauge according to the invention, for use in the fibrous web manufacturing system and process of FIGS. 2 and 3 in place of the measurement gauge 10, will be described. FIGS. 5 and 6 show a scattered light infrared measurement gauge 50 whose geometry is largely conventional but in which the individual design of a significant number of the illustrated elements has been modified according to the invention. The geometry of the measurement gauge 50 will therefore be described first.

The measurement gauge 50 includes a halogen lamp 52 providing a source of white light. The light from the lamp 52 is directed towards a condenser mirror 54, which focuses the light into a beam striking a wavelength selection device 56, which in this instance is a filter wheel driven in a conventional manner by a motor (not shown). The filter wheel 56 carries a series of filters, for example 8 filters, and each filter is designed to pass a different selected narrowband emission waveband in the infrared range of wavelengths so that in operation plural discrete wavelength bands are passed in any measuring operation. For any particular measuring operation, the spectral characteristics of each of the filters are selected based on the specific multiple spectral characteristics of the fibrous material whose parameters are to be be measured. Some of the selected wavelengths will lie in non-absorbing areas of the absorption spectrum for that material, while others will lie in areas of absorption. Still other wavelengths may lie in regions of the spectrum that arise due to scatter from fillers and fibre structures.

The light, ie discrete waveband, passed by each respective filter is directed towards a beam splitter 58, which reflects a portion of the light beam by way of a lens 60 onto a calibration detector 62, and which transmits a portion of the light beam by way of a further lens 64 towards an angled mirror 66. The mirror 66 turns the light beam through 90 degrees and directs the light beam downwardly by way of another lens 68 towards a fibrous web of sheet material 70 whose parameters are being measured. The axis of the light beam is perpendicular to the web 70 and the light beam passes through the web 70, which transmits a portion of the light directly and which scatters the remaining light, as shown.

It is a feature of the invention that the directly transmitted light, and preferably a small angle of the scattered light, falls on an element 72 acting as a beam stop for separating the directly transmitted light from the scattered light. A halo of the scattered light falls conventionally on a collecting mirror 74, which reflects the light towards a focussing mirror 76 situated immediately behind the beam stop 72. The mirror 76 in turn focuses the light on a scattered light measurement detector 78 mounted on the surface of the mirror 74. The beam stop 72, the collecting mirror 74, the focussing mirror 76 and the detector 78 all lie on the axis of the projected beam striking the web 70, but the beam stop 72 ensures that only scattered light is collected by the detector 78.

According to the invention, the element 72 serves to differentiate the direct transmission light from the scattered light, following which the scattered light is detected and measured. According to the preferred embodiment of the invention, also, the infrared radiation emitted by the filter wheel 56 lies in the waveband 1 to 5 µm. It is to be noted that this waveband is extended by comparison with the wavebands normally employed in a conventional direct transmission infrared measurement gauge, such as that shown in FIG. 4, in which the waveband typically commences in the NIR range and extends partially into the MIR range and is generally approximately 1 to 4 µm, and is significantly extended by comparison with the wavebands normally employed in a conventional scatter based infrared measurement gauge, in which the waveband lies in the NIR range and is normally 1 to 2.5 µm. For this purpose, a number of modifications are required to the various elements employed in the measurement gauge, as follows.

Firstly, the filters normally employed in the filter wheel 56 are supplemented to include additional filters arranged to pass infrared light in the wavelength range 2.5-5 µm, and especially in the range >3.5 µm. In the filter wheel 56 in the present invention, there are thus at least one filter passing infrared light in the area <2.5 µm which is known for scatter based measurement gauges, and at least one filter passing infrared light in the area >2.5 µm preferably >3.5 µm, which is new for scatter based measurement gauges. The remaining six filters may be arranged to pass light anywhere in the range 1-5 µm depending on the particular application.

In order to deal with the extended wavelength range, the material of the various optical elements, with the possible exception of the mirrors, must also be altered, since the glass that is conventionally employed in the lenses and beam splitters of the optical system does not transmit infrared light at the higher wavelengths. Accordingly, in the invention, the lenses 60, 64, 68 and the beam splitter 66 are instead made of calcium fluoride or sapphire, which although more expensive provide significantly greater light transmission and hence greater measurement accuracy.

Furthermore, the lead sulphide detectors previously employed for the detectors 62 and 78 are incapable of providing detection measurements at the longer wavelengths and therefore, in the invention, detectors having extended range capabilities are used. Such detectors may, for example, be lead selenide, indium antimonide, or mercury cadmium telluride detectors.

In use, the reference detector 62 and the measurement detector 78 respectively generate analogue electrical signals representing the intensity of the received light, which in the case of the detector 62 represents the intensity of the projected light and in the case of the detector 78 represents the intensity of the light as affected by the web 70. As shown in FIG. 6, these electrical signals are supplied to, and are amplified by, associated amplifiers 80, following which they are demodulated in a signal demodulation circuit 82. The circuit 82 separates out the signals representing the light passed by each of the different filters of the filter wheel 56, determining which signal pulses relate to which filter, and extracts the wavelength information relating respectively to each filter and the corresponding narrowband wavelength. The circuit 82 also performs analogue to digital conversion of the respective signals.

The digital signals are then supplied to a processor 84, which normalises the measurement signals on the basis of the calibration signals from the detector 62 and the reference signals from the detector 78 in a conventional manner and which then produces wavelength data signals for output to a calculation circuit 86. The calculation circuit 86 applies known algorithmic techniques to the wavelength data signals for evaluating the parameters being measured. The results of such calculation are output as digital values, representing eg moisture content or basis weight, to an output circuit 88 for smoothing and averaging the results and converting the calculation values into a suitable form for output. The output circuit then supplies the output to a display or other output means 90, which may be the profile processing and display system 11 of FIG. 2 for feedback purposes for process control and/or for feed forward purposes for quality control.

Accordingly, by combining the spectral data obtained from some or all of the filters, measurements for different parameters of the fibrous material, such as basis weight, can be realised. A key advantage of using multiple specific wavelengths is that this allows responses at different wavelengths to be combined and compared to eliminate ambient variations and underlying extraneous influences that would otherwise effect a simple single wavelength band optical measurement. For example:

Scatter effects, as a result of fillers in the fibrous material etc, affect the absorbance characteristics of the material. By adding additional wavelengths to track changes due to such effects, the influence of fillers etc can be eliminated.

Certain external variations can be compensated by comparing the relative spectral data signals from absorbing and non-absorbing regions of the absorption spectrum employing a mathematical ratio function. By way of example only, it is thereby possible to eliminate the effect of dust contamination on filter windows, since both wavelengths are affected by the contamination whereas the material absoprtion wavelengths alone are strongly affected only by the material absorption characteristics.

Similarly, interfering environmental effects, such as atmospheric humidity and moisture, can be corrected and eliminated using the same approach, by selecting multiple wavelengths that are respectively adversely affected or unaffected, in order either to factor out the interference or to obtain a measurement for the interference that can then be included in the final algorithm to provide real time desensitisation.

Using multiple wavelengths also provides a means to differentiate between the different optical spectra of different components within the material, enabling the measurement of multiple parameters, such as basis weight and moisture, additives and, in some cases of blended polymer, the blending proportions.

Accordingly, the embodiment of FIGS. 5 and 6 comprises a scattered light infrared measurement gauge which, by comparison with conventional scattered light measurement gauges, employs an extended wavelength range of infrared light from 1 to 5 μm, that is both in the near infrared (NIR) range and in the mid infrared (MIR) range.

It has been found, in experimental testing, that such a measurement gauge according to the invention displays very significantly improved results in the measurement of parameters of fibrous web material, by comparison with conventional infrared measurement gauges, whether of the direct transmission variety or the scattered light variety. The improved results apply particularly to the measurement of parameters of lightweight webs, typically having basis weights of 5 to 30 gsm, in which the proportion of void to fibre mass is substantial and in which the fibre diameter is small and may often be less than 10 to 20 μm.

The description of FIG. 1 above demonstrates why scattered light measurement is advantageous in the case of fibrous webs. The advantages of extending the wavelength range and the significantly improved performance of the infrared detection gauge according to the invention will now be discussed below with reference to FIGS. 15 to 18.

Figure 15:
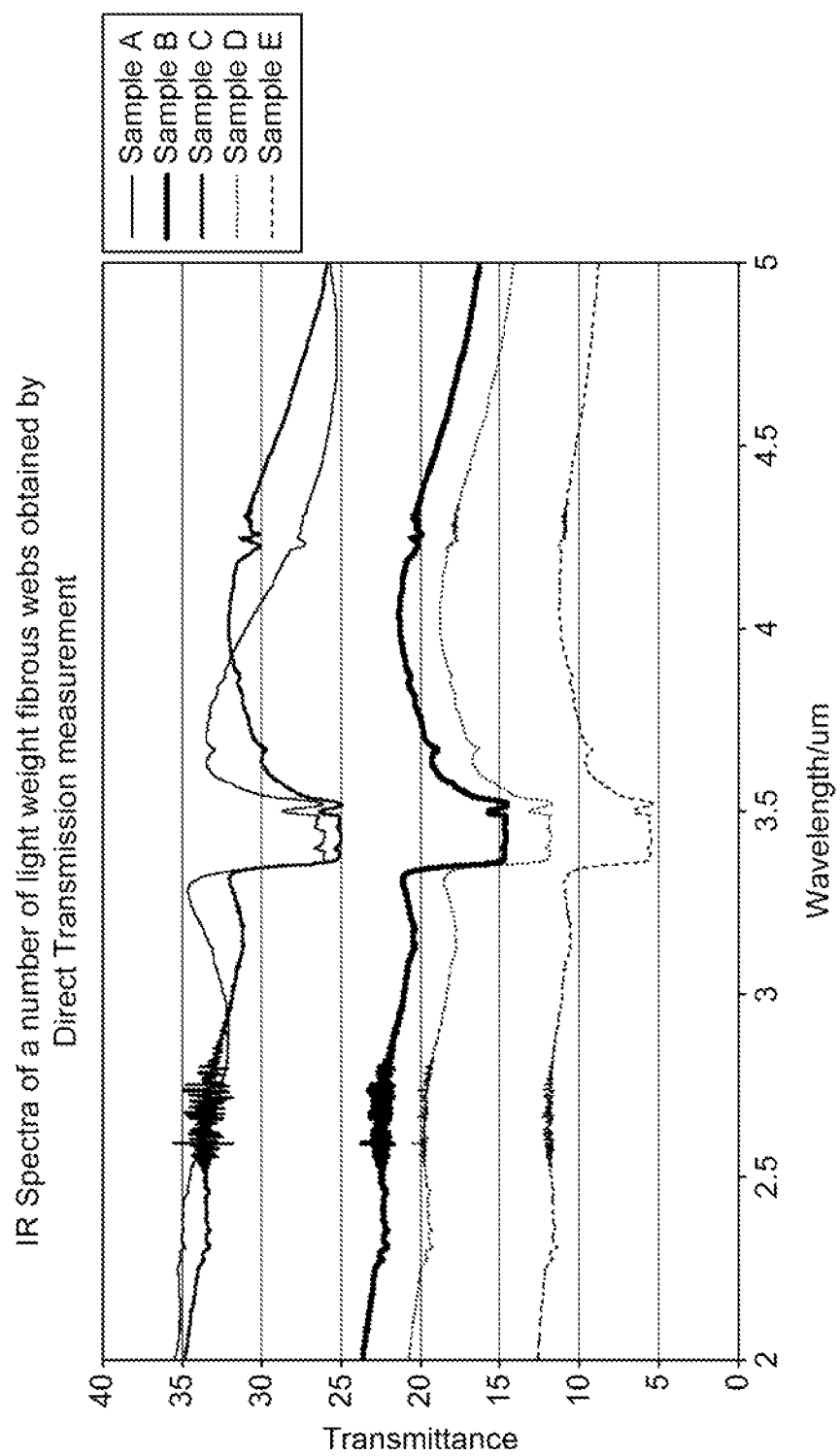
FIG. 15 is a graph showing results obtained using a conventional direct transmission light measurement gauge and different samples of lightweight fibrous web.

FIG. 15 is a graph showing different infrared spectra obtained using a conventional direct transmission detection gauge applied to the measurement of the basis weight of five different samples of lightweight fibrous web having basis weights in the range 5 to 30 gsm. Such conventional direct transmission detection gauge employs measurement wavelengths in the range 1 to 4 μm. In each case, the basic curve has a wavy signal form imposed on it as a result of optical interference and associated effects caused by individual fibres and fillers, and such interference effects occur primarily when the wavelength approaches the order of the fibre diameter. Furthermore, the measurements are distorted by the uncertainty as to whether the light detected arises from absorption by the fibres or from direct passage through voids in the web.

Figure 16:
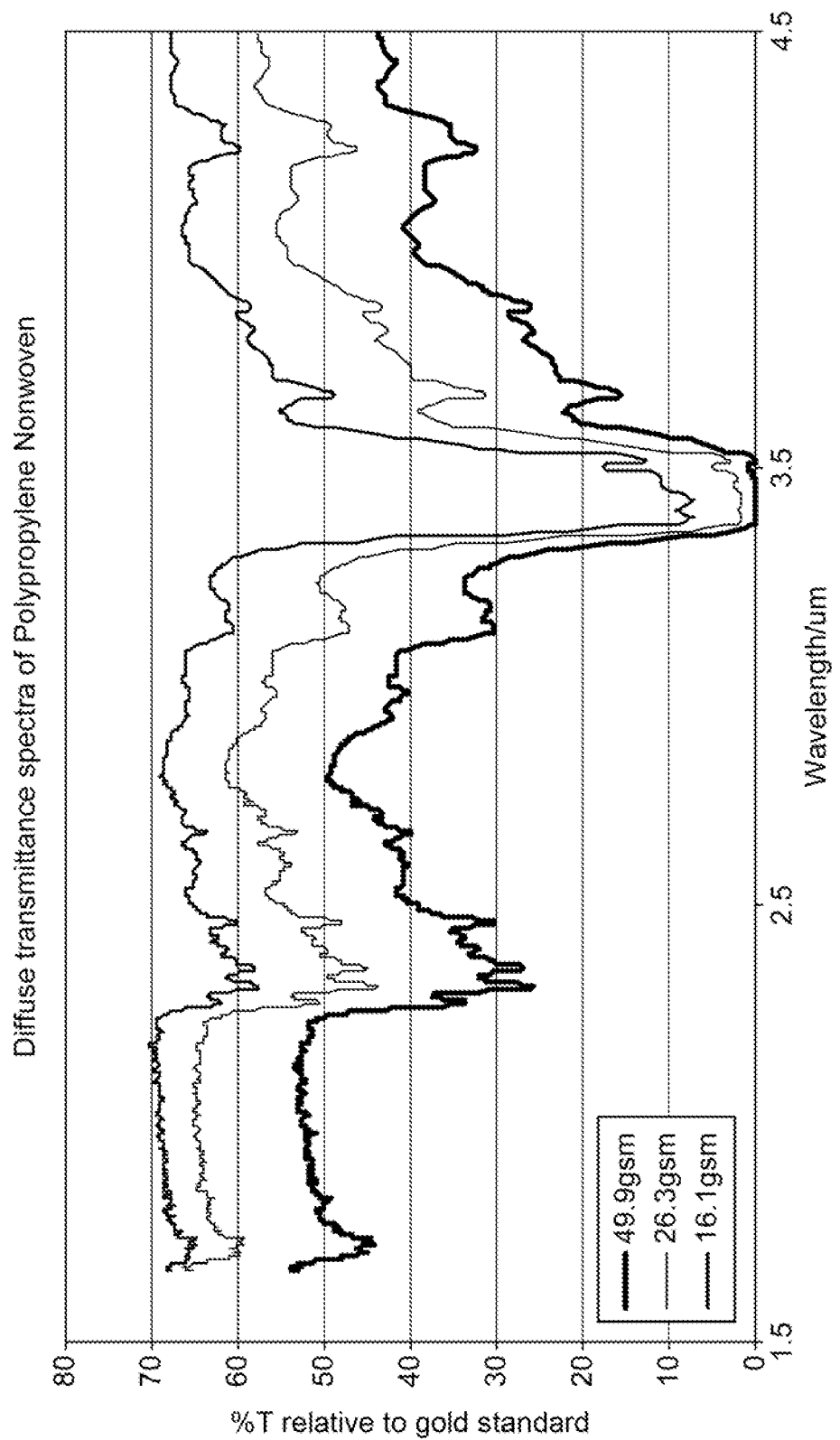
FIG. 16 is a graph showing results obtained using a measurement gauge according to the invention with different weights of a polypropylene non-woven web.

By contrast, FIG. 16 shows a similar result obtained for three different weights of a fibrous web of a polypropylene non-woven sheet material employing scattered light measurement according to the present invention. It will be seen that a very much clearer detection pattern emerges, since the light that has passed through the web with little or no interaction and that would otherwise dilute the spectral characteristics has been rejected, or in further embodiments yet to be described may have been measured separately and employed in the measurement calculation to enhance the measurement results.

Measurement preferably takes place in the strong absorption region, ie at approximately 3.4 μm in the example of FIG. 16, which concerns polymers, and approximately 2.95 μm for water, since this area offers high sensitivity to small changes and minimises the effects of other artefacts by comparison with the use of shorter wavelengths. Such measurements are relatively insensitive to scattering caused by fillers etc.

Figure 17:
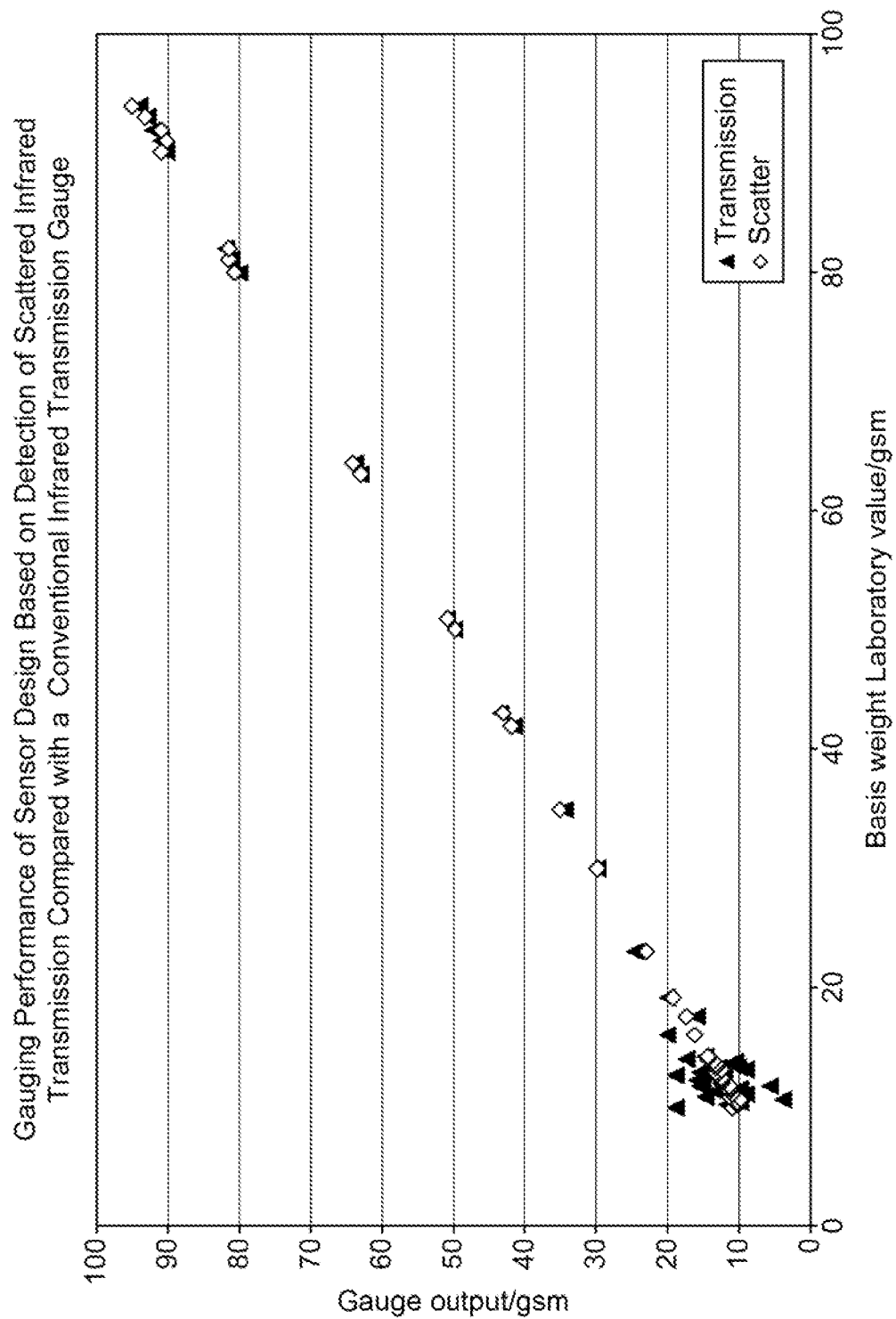
FIG. 17 is a graph comparing results obtained respectively using a scattered light measurement gauge according to the invention and using a conventional direct transmission light measurement gauge.

FIG. 17 compares the performance of a measurement gauge according to the invention employing scattered light detection with that of a conventional infrared measurement gauge employing direct transmission light detection. As shown, the results are comparable and fairly similar for fibrous webs having a basis weight greater than 30 gsm. However, below this weight, i.e. in the case of lightweight fibrous webs having a basis weight in the range 5 to 30 gsm, it can be seen that the measurement of scattered light according to the invention is coherent and consistent and linear with the remaining scattered light measurements, whereas the measurement of the transmitted light by conventional techniques produces a very variable and unpredictable result.

Figure 18:
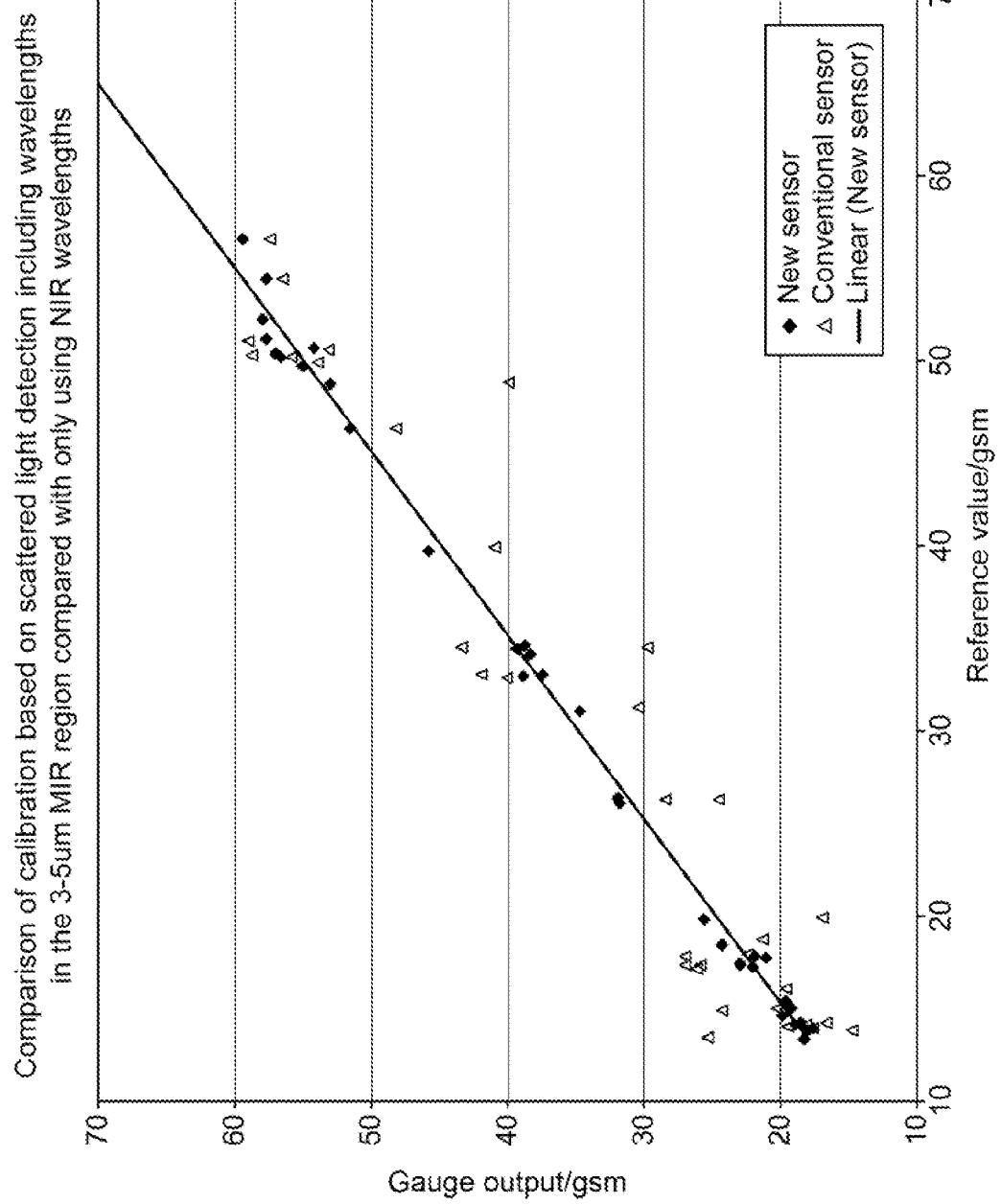
FIG. 18 is a graph comparing results obtained respectively using a scattered light measurement gauge according to the invention and using a conventional scattered light measurement gauge.

FIG. 18 compares the performance of a measurement gauge according to the invention employing scattered light detection with that of a conventional infrared measurement gauge employing scattered light detection. The measurement gauge according to the invention includes wavelengths throughout the 1 to 5 μm range with at least some of the wavelengths employed being in the range 3 to 5 μm, whereas the conventional measurement gauge employs wavelengths only in the range 1 to 2.5 μm. As shown, the results obtained from the measurement gauge according to the invention are consistent and linear while the results obtained from the conventional measurement gauge are very variable and unpredictable.

Figure 7:
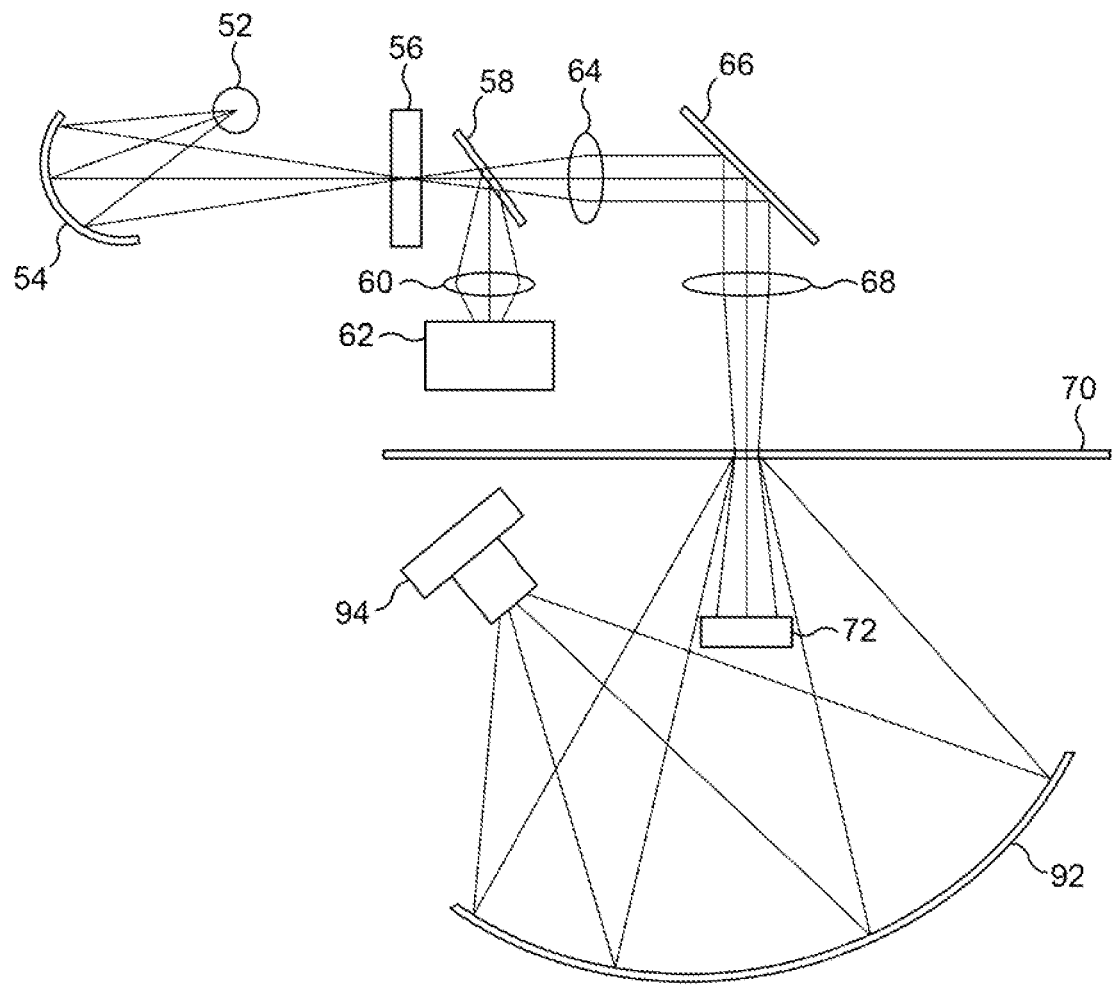
FIG. 7 is a diagram of a second embodiment of the invention employing a scattered light detector.

A second embodiment of the invention is shown in FIG. 7. This embodiment is similar in a number respects to the first embodiment of FIGS. 5 and 6. Like parts are designated by the same reference numerals and will not be described further. Only the features which are different from the first embodiment will be discussed, for the sake of simplicity.

The second embodiment includes all the features of the first embodiment, with the exception that the collecting mirror 74 is replaced by an asymmetric collecting mirror 92, which is also asymmetrically located relative to the axis of the beam of light projected towards, and partially directly transmitted through, the web 70, such that its focus is offset relative to the axis of the light beam. Consequently, the light reflected by the mirror 92 is not directed back towards the rear side of the beam stop 72 but instead is deflected towards a measurement detector 94 situated at the side of the beam stop 72 and having a central axis at an acute angle relative to the plane of the web 70.

One advantage of the second embodiment is that the measurement detector 94 is moved to one side and away from the axis of the projected light beam, and this permits a more compact arrangement, or lower profile, than in the case of the first embodiment. Another advantage arises when a temperature stabilised Peltier cooled detector is employed for the measurement detector 94, since removal of the detector from within the region of the scattered light falling on the mirror 92 facilitates location of the components necessary for operation of the Peltier cooler. In other respects however, the performance of the second embodiment is similar to that of the first embodiment.

Figure 8:
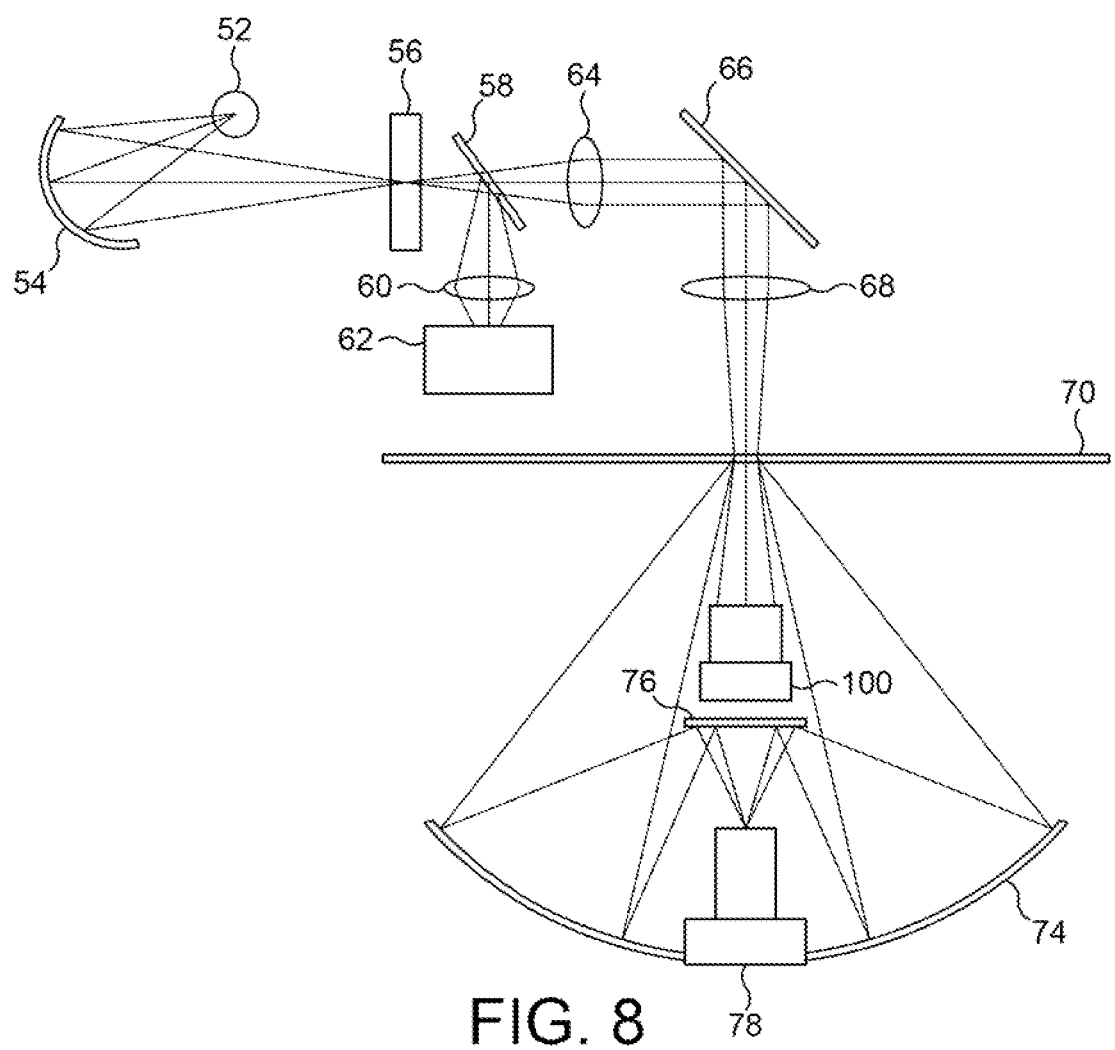
FIG. 8 is a diagram of a third embodiment of the invention employing a scattered light detector and a direct transmission light detector.

A third embodiment of the invention is shown in FIG. 8, and is a variant on the first embodiment, incorporating not one measurement detector but two. Again, like parts are designated by the same reference numerals and will not be described further. Only the differences will be mentioned.

In the case of the third embodiment, a collecting mirror 74 and a focussing mirror 76 situated on the axis of the projected light beam focus light onto a scattered light measurement detector 78 in precisely in the same manner as in the first embodiment. However, in this case, the beam stop 72 of the first embodiment is here replaced by an alternative light separating element in the form of a direct light measurement detector 100 situated directly on the axis of the projected light beam for picking up and measuring the proportion of the light that is directly transmitted, and optionally also a very narrow angle of the scattered light.

This embodiment of the invention differentiates the directly transmitted light from the scattered light in the same way as in the first embodiment, by employing a separating element to stop the directly transmitted light from reaching the detector 78, but in addition offers a significant further advantage in that not only is the scattered light detected but also the directly transmitted light. This allows comparative measurements to be taken and adjustments to be made to remove the effects of interference patterns. In particular, the measurements obtained from the directly transmitted light may be employed as a scaling function to compensate or adjust the measurements obtained from the scattered light when the measurement gauge is employed for different product types. This allows the measurement gauge to have a wider application with only minimal adjustment and without the need for costly re-calibration.

A variation of the third embodiment is illustrated in FIG. 9, again employing a scattered light measurement detector and a direct transmission light measurement detector. In this instance, however, the direct light transmission detector is differently situated. As before, like parts are designated by the same reference numerals and only the difference will be described.

In this fourth embodiment, the light from the projected light beam that is directly transmitted through the web 70 falls on a lens 102 for focussing the light beam onto an angled mirror 104 for diverting the light beam through 90° sideways to a direct transmission light measurement detector 106 situated at the side of the collecting mirror 74 away from the axis of the projected light. Here, the lens 102 and mirror 104 function as the light separating element. The light measurement is exactly the same as in the third embodiment, but the off-centre situation of the measurement detector 106 again has advantages in terms of improved thermal management of the detector when a Peltier cooled detector is employed, as already stated. A further advantage of this arrangement is that a more compact arrangement for the overall measurement gauge is possible since the necessary spacing between the web 70 and the direct light transmission measurement detector 106 can be achieved without increasing the vertical distance between web 70 and the detector 106.

Figure 10:
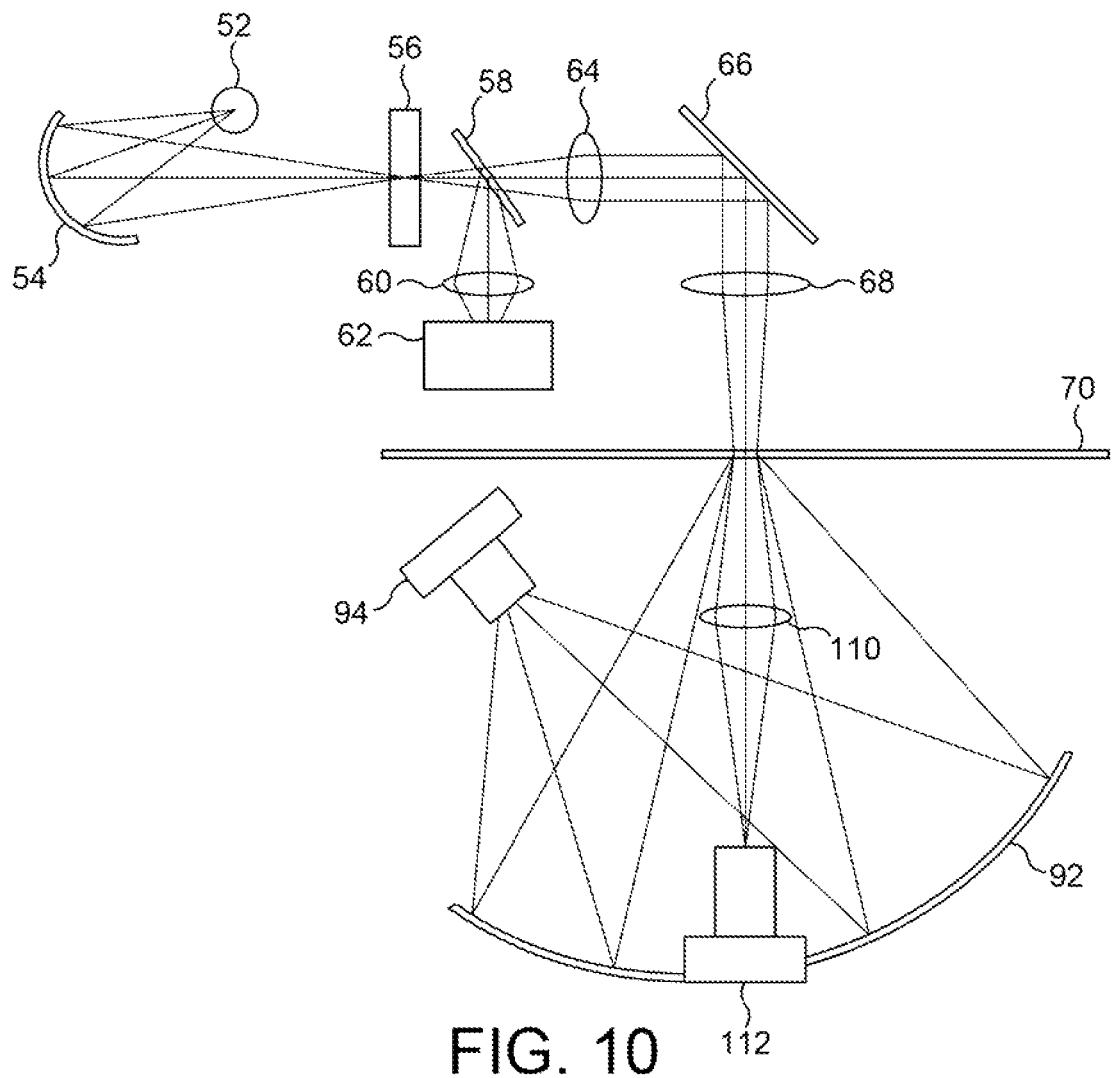
FIG. 10 is a diagram of a fifth embodiment of the invention employing a scattered light detector and a direct transmission light detector.

FIG. 10 shows a fifth embodiment of the invention, which is a variant on the second embodiment shown in FIG. 7 but which, in contrast with the second embodiment, includes a direct light transmission measurement detector as well as a scattered light measurement detector. As before, like parts are designated by the same reference numerals and will not be further described. Only the differences will be mentioned.

Accordingly, the fifth embodiment includes the off-axis asymmetric collecting mirror 92, which directs the scattered light towards the scattered light measurement detector 94. In addition, however, the beam stop 72 situated in the path of the directly transmitted light is replaced by a lens 110, which directs the light towards a direct light transmission measurement detector 112 carried by the collecting mirror 92. The lens 110 here serves as the light separating element.

Figure 9:
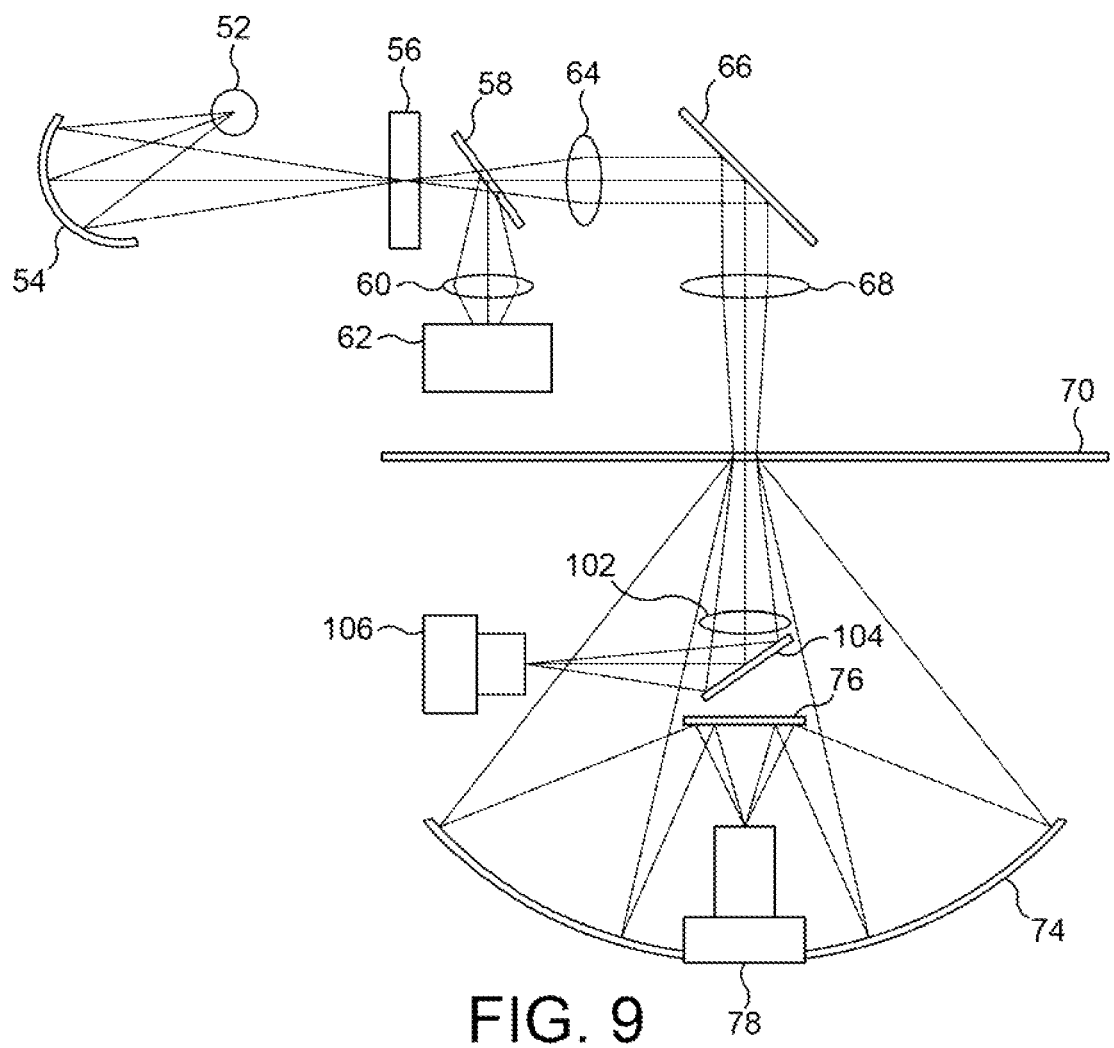
FIG. 9 is a diagram of a fourth embodiment of the invention employing a scattered light detector and a direct transmission light detector.

The present embodiment possesses the same advantages as the FIG. 7 embodiment of compactness of arrangement permitted by the use of an off-axis measurement detector for the scattered light, and in addition possesses the further significant advantage of combining both scattered light measurement and direct transmission light measurement, as in the case of the fourth embodiment of FIG. 9.

Figure 11:
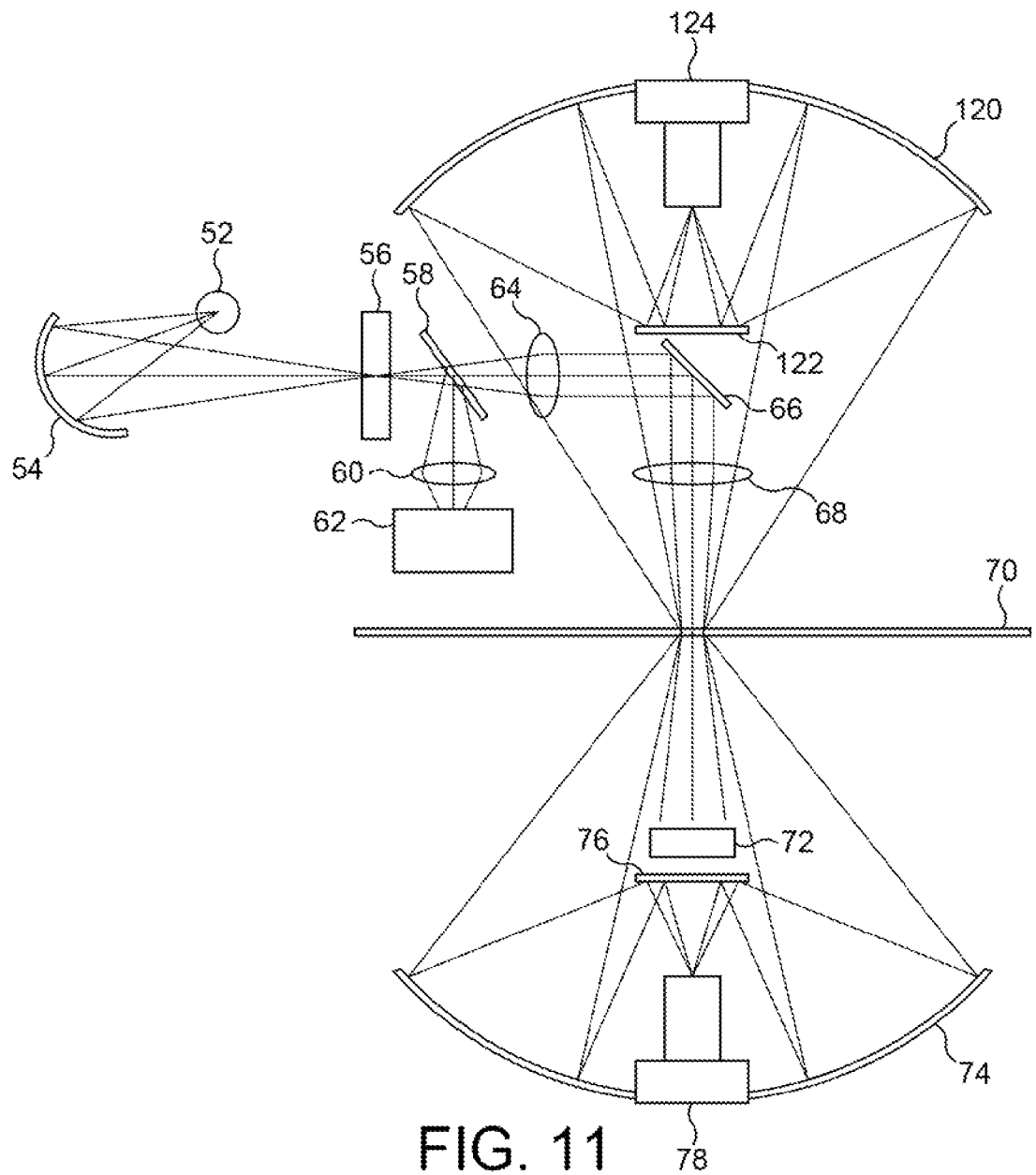
FIG. 11 is a diagram of a sixth embodiment of the invention employing a scattered light detector and a reflected light detector.

A further variation on the first embodiment of FIGS. 5 and 6 is shown in FIG. 11 in which a sixth embodiment of the invention is illustrated. This embodiment again adds a second measurement detector to the basic scattered light measurement detector 78 of the first embodiment. However, in this instance, the second measurement detector is situation on the same side of the web 70 as the projected light beam, and therefore is designed to measure reflected light rather than light passing through the web 70. As before, like parts will be designated the same reference numerals and only the differences will be described.

As shown in FIG. 11, the sixth embodiment includes a second collecting mirror 120 centred on the axis of the projected beam striking the web 70 but above the angled mirror 66 on the same side of the web 70 as the projected beam. A halo of light reflected from and scattered by the fibres of the web 70 without passing through the web strikes the collecting mirror 120, which directs such light towards a focussing mirror 122 behind the angled mirror 66 and thence onto a reflected light measurement detector 124 carried by the mirror 120.

This embodiment has the advantage of adding a diffuse reflectance measurement channel to the basic version of the invention shown in FIGS. 5 and 6. Such measurements are affected by the surface of the web, and this facilitates surface coating measurement where a surface treatment has been applied and/or allows corrections to be made for variations in fibre coverage within the illuminated area of the fibrous web 70.

Figure 12:
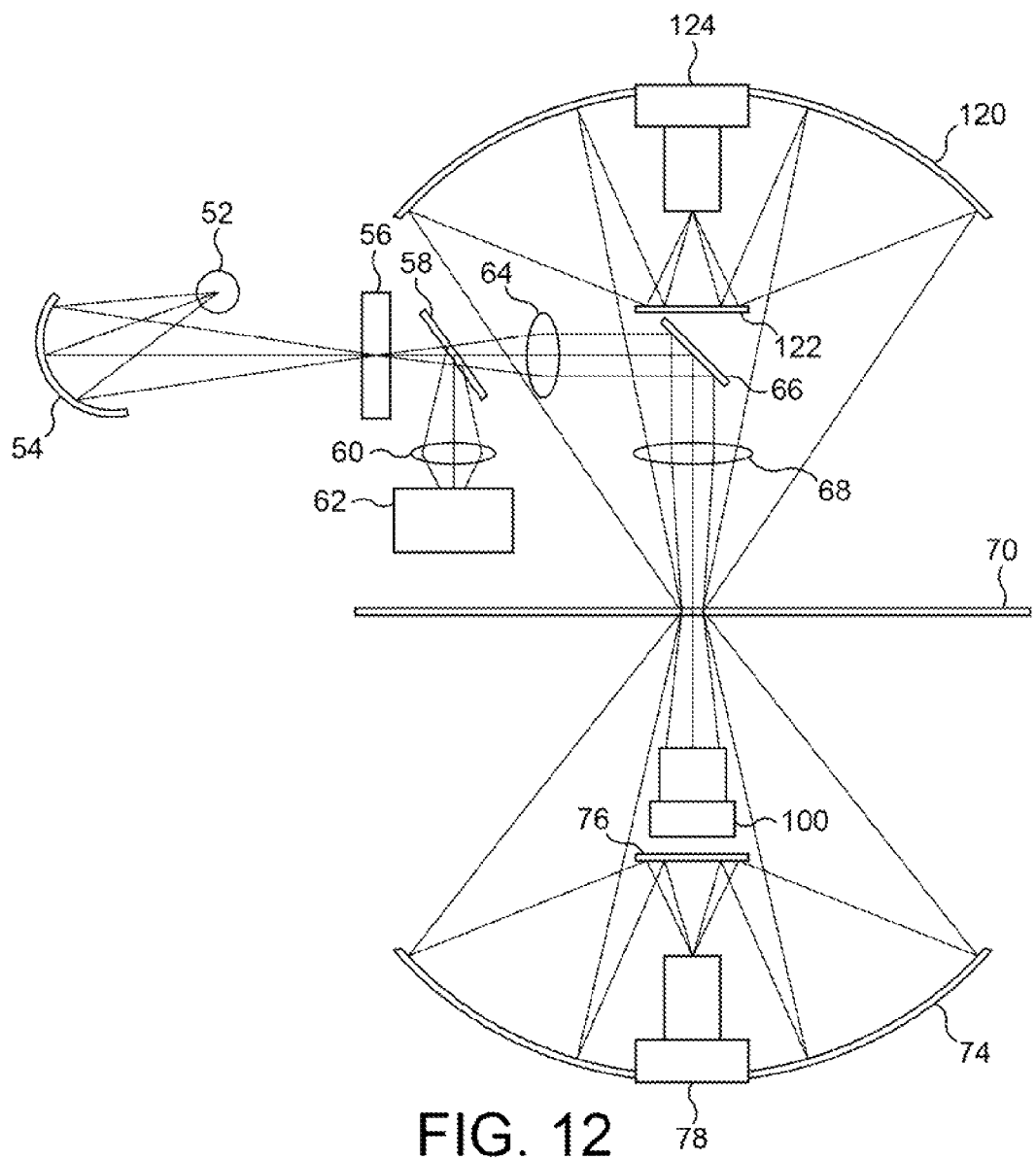
FIG. 12 is a diagram of a seventh embodiment of the invention employing a scattered light detector, a direct transmission light detector and a reflected light detector.

A further, seventh, embodiment is shown in FIG. 12 and combines the features of the third embodiment of FIG. 8 and the sixth embodiment of FIG. 11. Accordingly, the seventh embodiment employs both a scattered light measurement detector 78 and a direct light transmission measurement detector 100 on the side of the web 70 for detecting light that has passed through the web 70, and a reflected light measurement detector 124 situated on the side of the web 70 of the projected light beam incident on the web 70. Like parts are designated by the same reference numerals, and the situation of all three measurement detectors 78, 100 and 124 has already described so that no further description is necessary.

Figure 13:
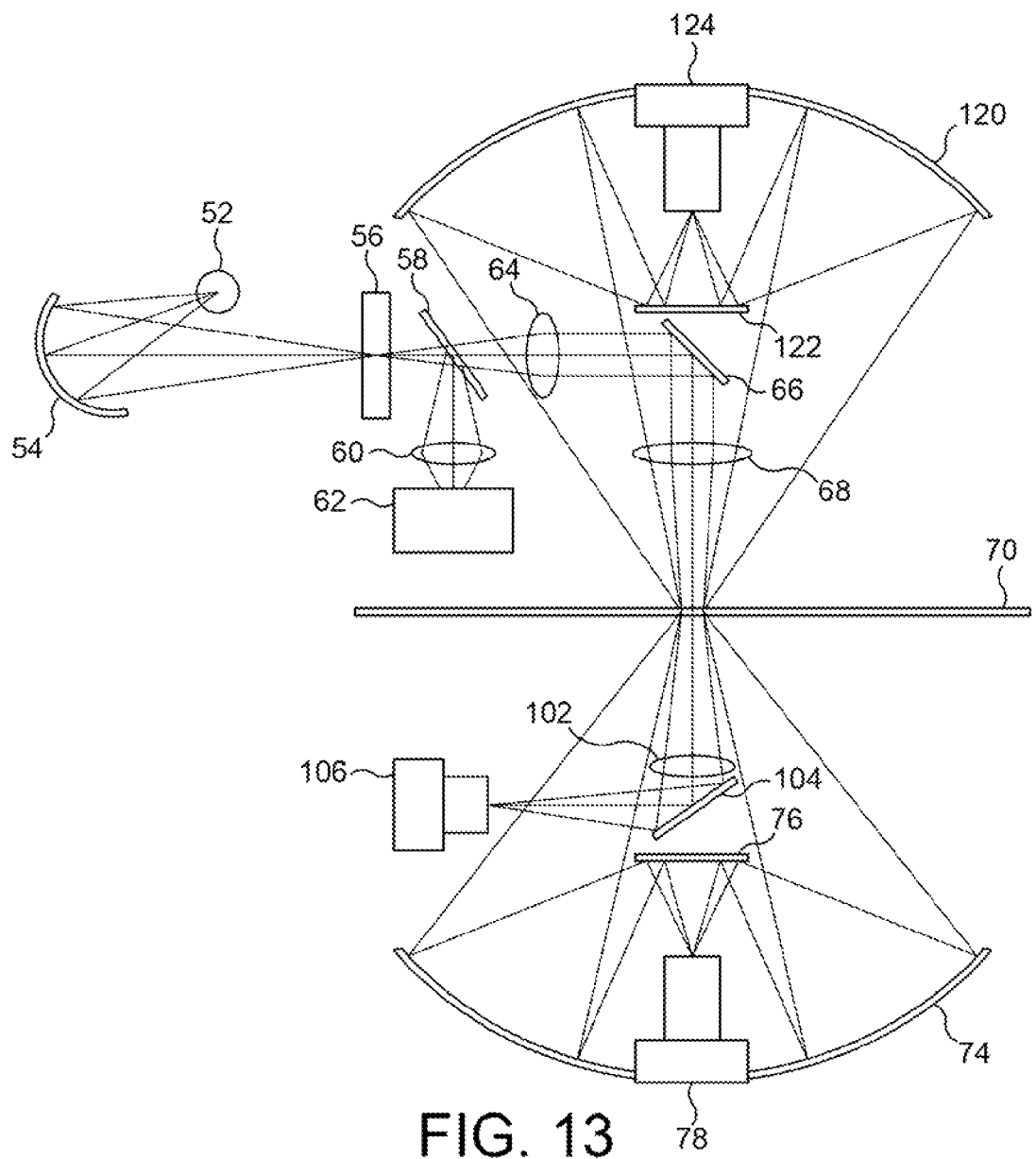
FIG. 13 is a diagram of an eighth embodiment of the invention employing a scattered light detector, a direct transmission light detector and a reflected light detector.

A further variation is shown in FIG. 13 illustrating an eighth embodiment of the invention, which combines the features of the fourth embodiment of FIG. 9 and the sixth embodiment of FIG. 11. Thus, the infrared gauge of FIG. 13 includes the scattered light measurement detector 78, the direct transmission light measurement gauge 106 and the reflected light measurement gauge 124. Like parts are designated by the same reference numerals, and the situation of all these measurement gauges has already been described so that no further description is necessary.

Figure 14:
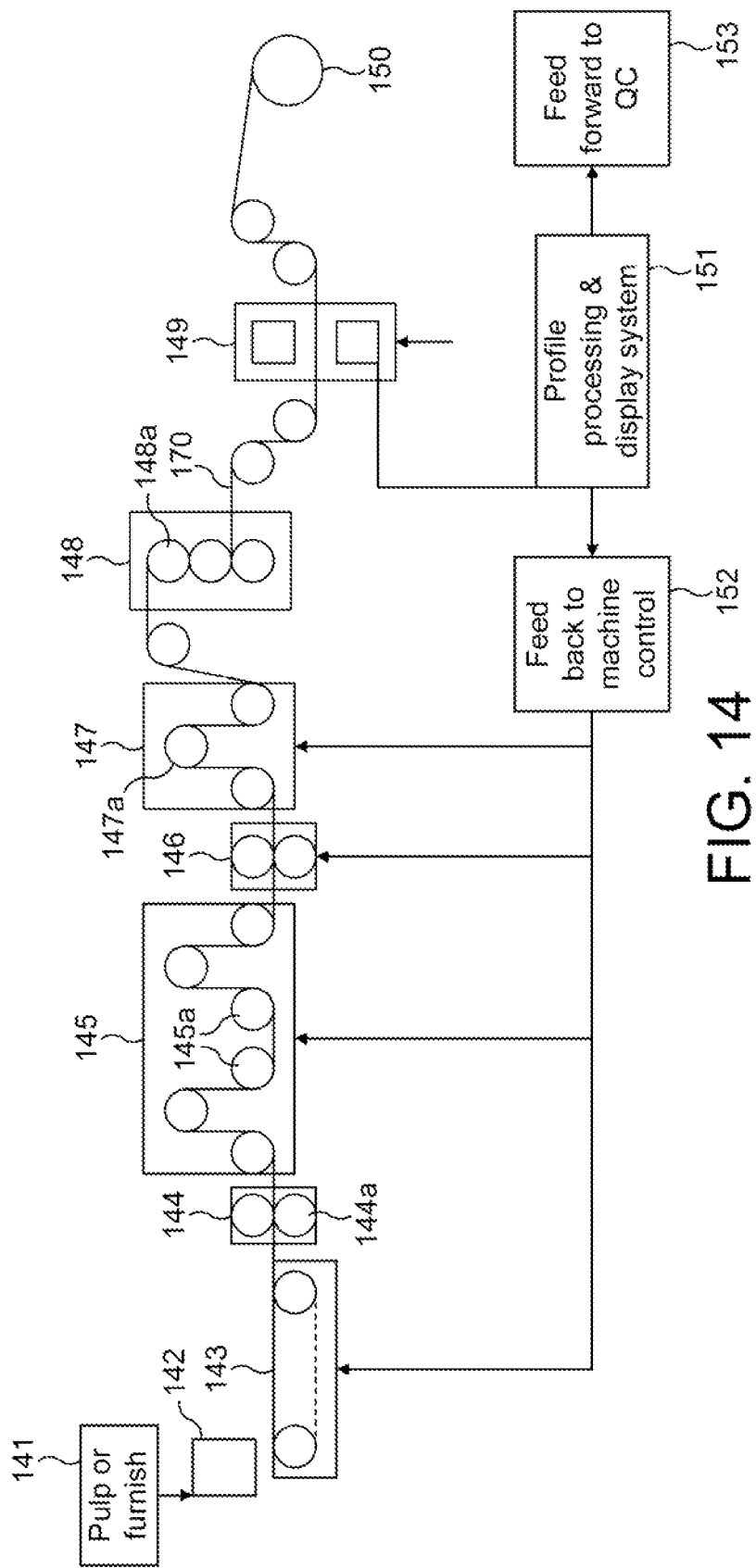
FIG. 14 is a schematic diagram of a further conventional fibrous web manufacturing process and system in which a measurement gauge according to the invention may be employed.

All of the described embodiments may be employed in a system for the dry laid forming of fibrous web as shown in FIGS. 2 and 3. They are also all suitable for use in a system for the wet laid forming of fibrous web as shown in FIG. 14. This system comprises a base sheet forming section 141 including a supply of pulp fibres which are fed to a head box 142. The head box 142 continually agitates the pulp to prevent the fibres from clumping together and deposits the wet fibres on a moving wire or belt 143. At this stage, the furnish is approximately 1% fibre and 99% water: it rapidly sheds water as it travels along the length of the moving belt 143 and the fibres begin to bond to form a mat or web 170. The wet web 170 passes into a press 144 where it is squeezed between a series of pressure rollers 144a to reduce the water content, and thence to a dryer 145 where each side of the web is in turn passed over a series of steam heated drying cylinders 145a. Depending on its intended end use, the web 170 may then be supplied to a treater/coater/moisturiser 146 and a dryer 147, where each side of the web is coated and dried in sequence, e.g. using infrared heat, hot air folds or drying cylinders 147a. After the dryer 147, or directly from the dryer 145 depending on application, the web 170 is passed to a calendaring stack 148 of rollers 148a to initiate the binding process and develop smoothness and gloss on the surface of the web by applying pressure and temperature to the (coated) material. Thus, according to the intended end use, the treater/coater/moisturiser 146 and the dryer 147 may be omitted. Following binding in the calendaring stack 148, the web 170 is supplied by way of a gauging zone 149 including a measurement gauge 50 as described to a winder 150 for forming the web 170 under tension into a roll.

As described with reference to FIG. 2, the measurement results obtained from the measurement gauge 149 are output to a profile processing and display system 151, and following processing a control output may be fed back by way of a control system 152 to any or all of the belt 143, the dryer 145, the treater/coater/moisturiser 146 and the dryer 147. Similarly, an output from the processing system 151 may be fed forward to a quality control system 153 for quality control purposes.

Having now described eight embodiments of the present invention, it will be apparent that numerous further developments and modifications are possible within the scope of the invention.

In particular, the light differentiating or separating element may be selected respectively to block, divert or focus the directly transmitted light, and optionally a small angle of the scattered light, in order to ensure that the scattered light that is measured is unaffected by interference patterns from the individual fibres of the web.

In addition, whilst the illustrated embodiments all show the wavelength selection device as being placed in the optical path before all of the detectors and before the fibrous web, it is equally possible for such device to be placed to receive light only after interaction with the fibrous web and optionally for a single such device to be replaced by a plurality of wavelength selection devices. In this instance, an intensity modulator may optionally be placed after the light source 52 and/or mirror 54 to aid signal detection.

By way of example, one possibility is to place a filter device in the optical path after interaction with the fibrous web, such that the light from each filter is directed at a single respective detector. Another possibility is to employ an array of filters situated immediately in front of each detector location with a corresponding array of detectors behind them.

It will be appreciated that different kinds of wavelength selection device may be used in place of the described filter devices, eg tunable filters, linear variable filters, wavelength dispersive devices such as prisms and diffraction gratings, wavelength encoding devices employing Fourier transform spectroscopy etc.

For example, a single tunable filter, such as an Acousto-optic tunable filter, a liquid crystal tunable filter, or a tunable etalon filter, may be employed in place of the described filter wheel 56, such tunable filter in use being sequentially cycled through the desired wavelengths for measurement purposes.

Single tunable solid state sources are also feasible and can combine and replace the functions of the light source 52 and the optical filtering provided by the filter wheel 56.

The wavelength selection may also be done at source by replacing the light source 52 and filter wheel 56 with multiple sources each emitting a desired wavelength, e.g. LEDs or lasers or separate white light sources and associated filters.

Alternative forms of wavelength selection device in the form of optically dispersive elements, such as tuning diffraction gratings and prisms, may also be employed.

The same approaches to wavelength selection can also be employed if the wavelength selection is placed on the detection side of the fibrous web 70 as mentioned above. For example, multiple detectors combined with wavelength selection devices, such as an array of filters, a linear variable filter, a prism, a diffraction grating or combination thereof, may be employed.

Further, the number and type (ie scattered light, directly transmitted light and reflected light) of the measurement detectors employed may be varied, and the positions of the different detectors on either the incident or the emergent light sides of the fibrous web 70 may be altered to place the measurement detectors respectively on or off the axis of the projected light beam.

Particularly, the illustrated embodiments all include reference detectors 62 for normalisation of the measurement signals, but these may be dispensed with and normalisation may instead take place against a reference standard stored electronically in the processor 84 shown in FIG. 6.

Furthermore, the collection mirrors in any of the described embodiments could be replaced by lens systems or other optical means for directing the scattered light onto the associated detector.

What is claimed is:

1. A method of measuring at least one parameter of a fibrous web, comprising:
   directing a beam of electromagnetic radiation towards the fibrous web;
   passing the beam of electromagnetic radiation through the fibrous web;
   wherein the electromagnetic radiation emerging from the fibrous web comprises directly transmitted electromagnetic radiation that constitutes electromagnetic radiation substantially directly transmitted through the fibrous web and scattered electromagnetic radiation that constitutes electromagnetic, radiation scattered by interaction with the fibrous web;
   selecting a first wavelength and a second wavelength for the electromagnetic radiation by means of a wavelength selection device, wherein the wavelength range of the wavelength selection device includes the near infrared (NIR) range of 1-2.5 µm and extends beyond the NIR range into the mid infrared (MIR) range of 2.5-5 µm, and wherein the first wavelength is in the mid infrared (MIR) range of 2.5-5 µm and the second wavelength is in the near infrared (NIR) range of 1-2.5 µm;
   differentiating the electromagnetic radiation emerging from the fibrous web into said directly transmitted electromagnetic radiation and said scattered electromagnetic radiation by means of a separating element interposed in the path of said directly transmitted electromagnetic radiation emerging from the fibrous web to create a halo of scattered electromagnetic radiation;
   collecting substantially all of said halo of scattered electromagnetic radiation with a focusing mirror directing the scattered electromagnetic radiation to a detector; and
   detecting the collected scattered electromagnetic radiation and generating electrical signals representing the collected scattered electromagnetic radiation.

2. A method according to claim 1 further comprising detecting the directly transmitted electromagnetic radiation.

3. A method according to claim 1 further comprising defining a direct transmission axis through the fibrous web and directing light to be detected away from the direct transmission axis for detection.

4. A method according to claim 1 further comprising collecting and detecting electromagnetic radiation that is reflected and scattered by the fibrous web.

5. A method according to claim 1 wherein plural discrete wavelength bands are selected by the wavelength selection device.

6. A method according to claim 1 employed for on-line measurement of at least one parameter of a fibrous web in a process for the continuous manufacture of fibrous web, wherein the electrical signals are processed to provide a measurement output, and wherein the measurement output is fed back to production apparatus for providing process control and/or is fed forwards to a quality evaluation system for providing quality control.

7. A method according to claim 1 further comprising detecting said directly transmitted electromagnetic radiation with a detector located between the separating element and the fibrous web.

8. A method according to claim 7, wherein the separating element comprises the detector.

9. Detection apparatus for use for measuring parameters of a fibrous web, comprising:
 optical elements for directing a beam of electromagnetic radiation towards and through the fibrous web, wherein the electromagnetic radiation emerging from the fibrous web comprises directly transmitted electromagnetic radiation that constitutes electromagnetic radiation substantially directly transmitted through the fibrous web and scattered electromagnetic radiation that constitutes electromagnetic radiation scattered by interaction with the fibrous web;
 a wavelength selection device for selecting a first wavelength and a second wavelength for the electromagnetic radiation, wherein the wavelength range of the wavelength selection device includes the near infrared (NIR) range of 1-2.5 µm and extends beyond the NIR range into the mid infrared (MIR) range of 2.5-5 µm, and wherein the first wavelength is in the mid infrared (MIR) range of 2.5-5 µm and the second wavelength is in the near infrared (NIR) range of 1-2.5 µm;
 an optical system for differentiating electromagnetic radiation that emerges from the fibrous web into said directly transmitted electromagnetic radiation and said scattered electromagnetic radiation;
 said optical system including a separating element arranged in the path of the directly transmitted electromagnetic radiation emerging from the fibrous web for creating a halo of scattered electromagnetic radiation, and a collector for collecting substantially all of said halo of scattered electromagnetic radiation; and
 at least one detector for detecting the collected scattered electromagnetic radiation and for generating an electrical signal representing, the collected scattered radiation;
 wherein the collector includes a focusing mirror that directs the scattered electromagnetic radiation to the at least one detector.

10. Apparatus according to claim 9 in which the separating element comprises a detector for detecting the directly transmitted electromagnetic radiation.

11. Apparatus according to claim 9 further comprising optical means for directing light to be detected away from a direct transmission axis through the fibrous web for detection.

12. Apparatus according to claim 9 further comprising a collector and a detector for electromagnetic radiation that is reflected and scattered by the fibrous web.

13. Apparatus according to claim 9 wherein the wavelength selection device is arranged to select plural discrete wavelength bands.

14. Apparatus according to claim 9 employed for on-line measurement of at least one parameter of a fibrous web in a system for the continuous manufacture of fibrous web, and comprising a processor for processing the electrical signals to provide a measurement output, and preferably further comprising at least one of a feedback system responsive to the measurement output for providing a control output to a production machine for providing process control and a feed forward system responsive to the measurement output for providing a control output to a quality evaluation machine for providing quality control.

15. Apparatus according to claim 9 further comprising a transmitted radiation detector located between the fibrous web and the separating element, the transmitted radiation detector detects the directly transmitted electromagnetic radiation and generates an electrical signal representing the directly transmitted electromagnetic radiation.

16. Apparatus according to claim 15 wherein the separating element comprises the transmitted radiation detector.

* * * * *